(12) United States Patent
Okada

(10) Patent No.: US 11,154,261 B2
(45) Date of Patent: Oct. 26, 2021

(54) RADIATION IMAGE CAPTURING APPARATUS AND RADIATION IMAGE CAPTURING SYSTEM

(71) Applicant: CANON KABUSHIKI KAISHA, Tokyo (JP)

(72) Inventor: Hideyuki Okada, Honjo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 16/845,197

(22) Filed: Apr. 10, 2020

(65) Prior Publication Data
US 2020/0359978 A1 Nov. 19, 2020

(30) Foreign Application Priority Data
May 17, 2019 (JP) .............................. JP2019-093913

(51) Int. Cl.
*A61B 6/00* (2006.01)
*G01T 1/17* (2006.01)
*G01T 1/24* (2006.01)

(52) U.S. Cl.
CPC ............ *A61B 6/4233* (2013.01); *A61B 6/542* (2013.01); *G01T 1/17* (2013.01); *G01T 1/247* (2013.01)

(58) Field of Classification Search
CPC ......... A61B 6/4233; A61B 6/542; G01T 1/17; G01T 1/247
See application file for complete search history.

(56) References Cited

U.S. PATENT DOCUMENTS

| | | | | |
|---|---|---|---|---|
| 5,949,393 A | * | 9/1999 | Sakai | H01J 31/127 345/74.1 |
| 7,436,444 B2 | * | 10/2008 | Endo | H04N 5/32 250/370.09 |
| 9,048,154 B2 | | 6/2015 | Takenaka et al. | |
| 9,128,196 B2 | | 9/2015 | Sato et al. | |
| 9,134,432 B2 | | 9/2015 | Iwashita et al. | |
| 9,234,966 B2 | | 1/2016 | Sugawara et al. | |

(Continued)

FOREIGN PATENT DOCUMENTS

| | | |
|---|---|---|
| JP | 2010-075556 | 4/2010 |
| JP | 2016-015721 | 1/2016 |

OTHER PUBLICATIONS

U.S. Appl. No. 16/103,150, Atsushi Iwashita, filed Aug. 14, 2018.

*Primary Examiner* — Blake C Riddick
(74) *Attorney, Agent, or Firm* — Venable LLP

(57) ABSTRACT

A radiation image capturing apparatus is provided. The apparatus comprises pixels, drivers to which row signal lines for driving the pixels for each row are respectively connected and a controller. The controller supplies, before radiation irradiation, selection signals to a driver group constituted by not less than two drivers which drive detection pixels, of the pixels, to cause each of the drivers included in the driver group to select a row signal line to which the detection pixels are connected, and the controller supplies, during radiation irradiation, a drive signal for driving pixels connected to a row signal line selected from the plurality of row signal lines to each driver included in the driver group to cause the radiation image capturing apparatus to acquire a signal for measuring a dose of radiation entering from each of the detection pixels.

19 Claims, 17 Drawing Sheets

(56) References Cited

U.S. PATENT DOCUMENTS

| | | | |
|---|---|---|---|
| 9,423,512 B2 | 8/2016 | Sato et al. | |
| 9,445,030 B2 | 9/2016 | Yagi et al. | |
| 9,462,989 B2 | 10/2016 | Takenaka et al. | |
| 9,468,414 B2 | 10/2016 | Ryu et al. | |
| 9,470,800 B2 | 10/2016 | Iwashita et al. | |
| 9,470,802 B2 | 10/2016 | Okada et al. | |
| 9,541,653 B2 | 1/2017 | Iwashita et al. | |
| 9,655,586 B2 | 5/2017 | Yagi et al. | |
| 9,675,307 B2 | 6/2017 | Ofuji et al. | |
| 9,737,271 B2 | 8/2017 | Iwashita et al. | |
| 9,812,474 B2 | 11/2017 | Yagi et al. | |
| 9,885,790 B2 | 2/2018 | Okada et al. | |
| 9,971,046 B2 | 5/2018 | Ryu et al. | |
| 9,980,685 B2 * | 5/2018 | Iwashita | A61B 6/542 |
| 9,989,656 B2 | 6/2018 | Sato et al. | |
| 10,349,914 B2 | 7/2019 | Takenaka et al. | |
| 10,352,765 B2 | 7/2019 | Okada et al. | |
| 10,416,323 B2 | 9/2019 | Ryu et al. | |
| 10,551,721 B2 | 2/2020 | Sato et al. | |
| 2004/0114719 A1 * | 6/2004 | Endo | H01L 27/14658 378/98.8 |
| 2007/0125952 A1 * | 6/2007 | Endo | G01T 1/17 250/369 |
| 2008/0013686 A1 * | 1/2008 | Kameshima | G01T 1/2018 378/98 |
| 2009/0323897 A1 * | 12/2009 | Kameshima | H04N 5/325 378/116 |
| 2011/0012817 A1 * | 1/2011 | Nakamura | G09G 3/3233 345/80 |
| 2011/0240873 A1 * | 10/2011 | Tsuji | G01T 1/247 250/394 |
| 2012/0181439 A1 * | 7/2012 | Cao | H04N 5/335 250/366 |
| 2013/0322597 A1 * | 12/2013 | Uchiyama | G01T 1/17 378/62 |
| 2013/0342514 A1 * | 12/2013 | Yokoyama | H01L 27/14603 345/204 |
| 2014/0008519 A1 * | 1/2014 | Kameshima | G01T 1/17 250/208.1 |
| 2014/0008544 A1 * | 1/2014 | Kameshima | H01L 27/14609 250/393 |
| 2014/0097348 A1 * | 4/2014 | Watanabe | H01L 27/14612 250/370.01 |
| 2014/0239186 A1 | 8/2014 | Sato et al. | |
| 2014/0241506 A1 * | 8/2014 | Iwashita | G01T 1/16 378/91 |
| 2014/0361189 A1 | 12/2014 | Kameshima et al. | |
| 2015/0090998 A1 * | 4/2015 | Hirase | H04N 5/363 257/40 |
| 2018/0063933 A1 | 3/2018 | Okada et al. | |
| 2018/0295294 A1 | 10/2018 | Kameshima et al. | |
| 2018/0306935 A1 * | 10/2018 | Nakano | G01T 1/17 |
| 2019/0029618 A1 | 1/2019 | Sato et al. | |

* cited by examiner

RADIATION IMAGE CAPTURING APPARATUS AND RADIATION IMAGE CAPTURING SYSTEM

BACKGROUND OF THE INVENTION

Field of the Invention

The present invention relates to a radiation image capturing apparatus and a radiation image capturing system.

Description of the Related Art

In medical image diagnosis and non-destructive examination, a radiation image capturing apparatus using an FPD (Flat Panel Detector) formed from a semiconductor material has been widely used. Such a radiation image capturing apparatus is known to measure radiation entering the radiation image capturing apparatus in real time. Detecting a radiation dose in real time can grasp the integrated dose of radiation entering during radiation irradiation and perform AEC (Automatic Exposure Control). At the time of performing AEC, a high time resolution is sometimes required. Japanese Patent Laid-Open No. 2010-75556 discloses a technique of continuously turning on detection elements set for AEC by continuously supplying high-level signals to a gate line to which the detection elements are connected from the start of irradiation. There is a possibility that the operation disclosed in Japanese Patent Laid-Open No. 2010-75556 can achieve a high time resolution because signals can always be acquired from the detection element. In addition, Japanese Patent Laid-Open No. 2016-15721 discloses a technique of excluding any sensor, of a plurality of sensors set for AEC, which exceeds a threshold in terms of a value corresponding to an output during radiation irradiation from an effective sensor group. Reducing the number of sensors constituting the effective sensor group can increase the sampling frequency.

SUMMARY OF THE INVENTION

When AEC is to be performed, a plurality of regions of interest are sometimes set. In the operation disclosed in Japanese Patent Laid-Open No. 2010-75556, high-level signals are always supplied to a gate line to which a detection element whose signals are used for AEC, and hence no signal can be acquired independently of the detection elements connected to gate lines other than the gate line to which the detection element used for AEC is connected. That is, according to the operation disclosed in Japanese Patent Laid-Open No. 2010-75556, when a plurality of regions of interest are to be set, it is necessary to use detection elements connected to the same gate line. This reduces the degree of freedom in setting regions of interest. According to the operation disclosed in Japanese Patent Laid-Open No. 2016-15721, although the degree of freedom in setting a plurality of regions of interest is high, there is a possibility that a complex circuit arrangement is required to acquire signals from an effective sensor group.

Some embodiments of the present invention provide a technique advantageous in acquiring signals from a plurality of regions of interest at high speed.

According to some embodiments, a radiation image capturing apparatus comprising: a plurality of pixels arranged in a matrix pattern to obtain a radiation image; a plurality of drive circuits to which a plurality of row signal lines for driving the plurality of pixels for each row are respectively connected; and a control unit configured to control the plurality of drive circuits, wherein the control unit supplies, before radiation irradiation, selection signals to a drive circuit group constituted by not less than two drive circuits, of the plurality of drive circuits, which drive detection pixels to cause each of the drive circuits included in the drive circuit group to select a row signal line, of the plurality of row signal lines, to which the detection pixels are connected, in order to set not less than two detection pixels for measuring a dose of radiation entering from the plurality of pixels during radiation irradiation, and the control unit supplies, during radiation irradiation, a drive signal for driving pixels connected to a row signal line selected from the plurality of row signal lines to each drive circuit included in the drive circuit group to cause the radiation image capturing apparatus to acquire a signal for measuring a dose of radiation entering from each of the detection pixels, is provided.

Further features of the present invention will become apparent from the following description of exemplary embodiments (with reference to the attached drawings).

DESCRIPTION OF THE EMBODIMENTS

Figure 1:
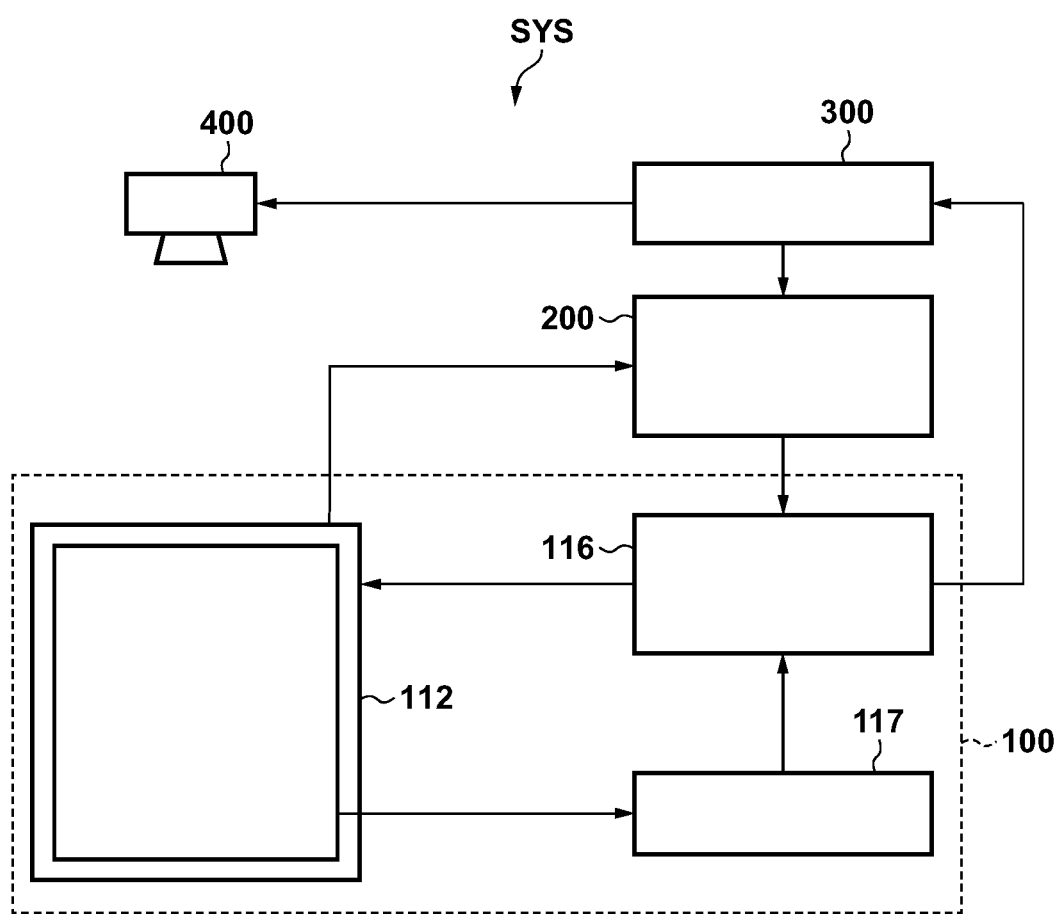
FIG. 1 is a block diagram showing an example of the arrangement of a radiation image capturing system using a radiation image capturing apparatus according to an embodiment.

Hereinafter, embodiments will be described in detail with reference to the attached drawings. Note, the following embodiments are not intended to limit the scope of the claimed invention. Multiple features are described in the embodiments, but limitation is not made an invention that requires all such features, and multiple such features may be combined as appropriate. Furthermore, in the attached drawings, the same reference numerals are given to the same or similar configurations, and redundant description thereof is omitted.

Note that radiation according to the present invention can include not only α-rays, β-rays, and γ-rays that are beams generated by particles (including photons) emitted by radioactive decay but also beams having energy equal to or higher than the energy of these beams, for example, X-rays, particle rays, and cosmic rays.

Radiation image capturing apparatuses according to some embodiments of the present invention will be described with reference to FIGS. 1 to 12. FIG. 1 is a block diagram showing an example of the arrangement of a radiation image capturing system SYS using a radiation image capturing apparatus 100 according to an embodiment. The radiation image capturing system SYS includes the radiation image capturing apparatus 100, a control computer 200, a radiation controller 300, and a radiation generator 400.

The radiation image capturing apparatus 100 includes a detection unit 112 that detects radiation, a computing unit 117 that computes electric charge information from the detection unit 112 and outputs exposure information, and a control unit 116 for controlling the driving of the detection unit 112 and radiation irradiation based on exposure information. The detection unit 112 has a plurality of pixels arranged in a matrix pattern, including sensors that detect radiation to obtain a radiation image, and outputs a signal corresponding to incident radiation. The computing unit 117 measures the dose of incident radiation based on the signal output from the detection unit 112 during radiation irradiation. As the computing unit 117, a digital signal processing circuit such as an FPGA, DSP, or processor may be used. The computing unit 117 may be formed by using analog circuits such as hold circuits and operational amplifiers. According to the arrangement shown in FIG. 1, the computing unit 117 is included in the radiation image capturing apparatus 100. However, the control computer 200 may have the function of the computing unit 117. The control unit 116 controls the detection unit 112 based on the signal input from the control computer 200. The control unit 116 can change the drive method for the detection unit 112 by using the exposure information output from the computing unit 117.

The control computer 200 controls the overall radiation image capturing system SYS. The control computer 200 can function as a user interface when the user (radiation technician) performs image capturing of a radiation image by using the radiation image capturing system SYS. For example, the user inputs image capturing conditions of a radiation image to the control computer 200. In accordance with the input image capturing conditions, the control computer 200 controls the radiation image capturing apparatus 100 and the radiation generator 400. The control computer 200 may include a signal processing unit that processes a signal for generating a radiation image output from the radiation image capturing apparatus 100. The control computer 200 processes a signal for generating a radiation image output from the radiation image capturing apparatus 100, and causes the display unit included in the control computer 200 or an external display to display the radiation image captured by the radiation image capturing apparatus 100.

The radiation controller 300 controls the radiation generator 400 in accordance with the signal output from the control computer 200. The radiation generator 400 applies radiation in accordance with the signal output from the radiation controller 300.

Figure 2:
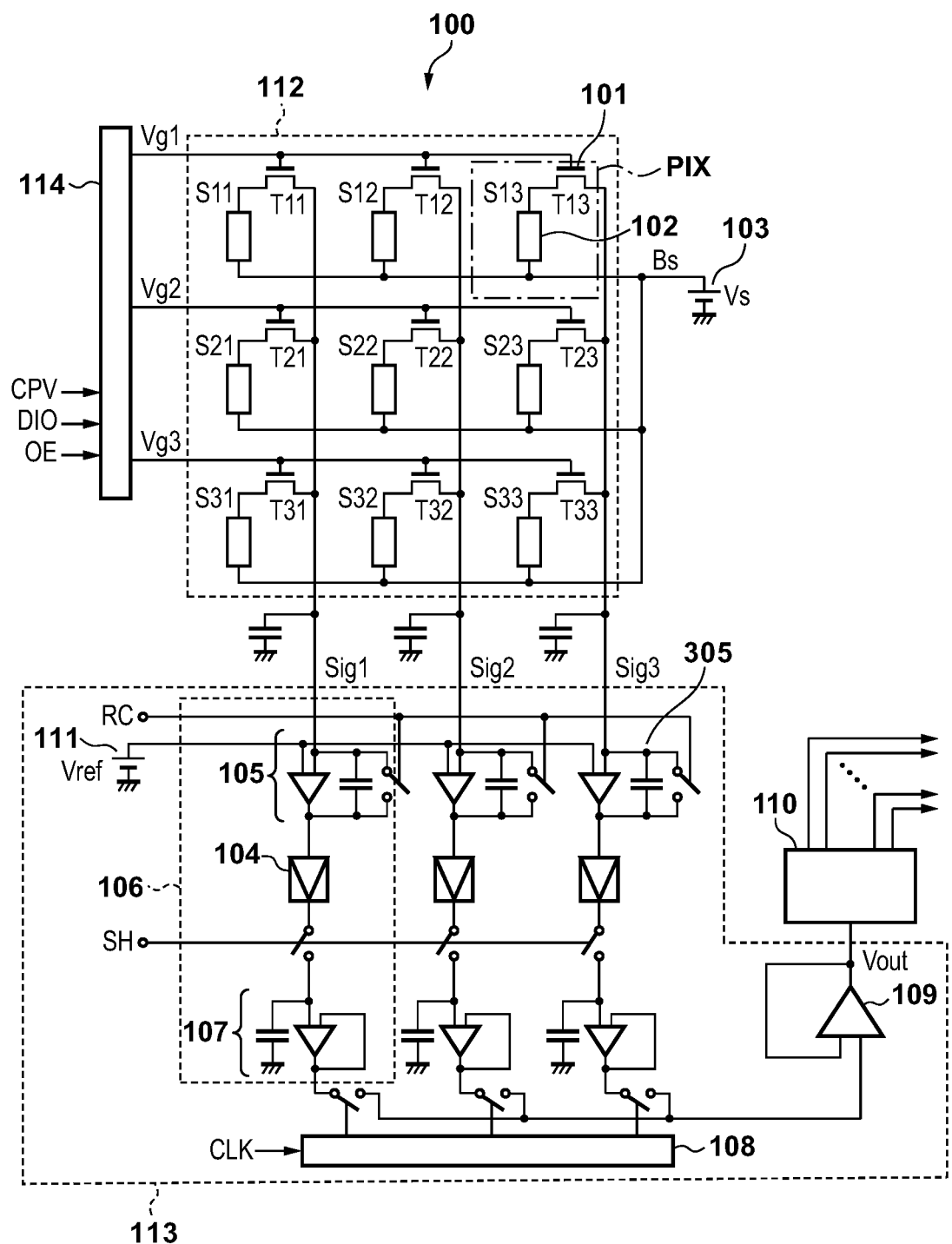
FIG. 2 is an equivalent circuit diagram showing an example of the arrangement of the radiation image capturing apparatus in FIG. 1.

FIG. 2 is an equivalent circuit diagram showing an example of the arrangement of the radiation image capturing apparatus 100. FIG. 2 shows the detection unit 112 including 3 row×3 column pixels for the sake of descriptive convenience. However, an actual radiation image capturing apparatus has more pixels. For example, a 17-inch radiation image capturing apparatus has about 3500 row×3500 column pixels.

The detection unit 112 is a two-dimensional detector having a plurality of pixels PIX arranged in a matrix pattern. Each pixel PIX includes a conversion element 102 that converts radiation into light or electric charge and a switch element 101 that outputs an electrical signal corresponding to the electric charge. In this embodiment, a MIS photodiode made of a semiconductor material such as amorphous silicon as a main material disposed on an insulating substrate such as a glass substrate is used as a photoelectric conversion element that converts light applied to the conversion element 102 into electric charge. However, a PIN photodiode may be used. The conversion element 102 also includes a wavelength converter such as a scintillator that converts radiation into light in a wavelength band that can be sensed by the photoelectric conversion element on the radiation incident side of the photoelectric conversion element. A wavelength converter may be arranged for each pixel PIX or may have an integral structure shared by a plurality of pixels PIX. The conversion element 102 is not limited to an indirect conversion element like that described above, and a direct conversion element that directly converts radiation into electric charge may be used as the conversion element 102. As the switch element 101, a transistor having a control terminal and two main terminals can be used. In this embodiment, as the switch element 101, a TFT (Thin-Film Transistor) can be used. One electrode of the conversion element 102 is electrically connected to one of the two main terminals of the switch element 101, and the other electrode is electrically connected to a bias power supply 103 via common bias wiring Bs. The control terminals of a plurality of switch elements 101 (for example, T11, T12, and T13) arrayed in the row direction are commonly electrically connected to a row signal line Vg1 on the first row. A drive circuit 114 supplies drive signals for controlling the conduction states of the switch elements 101 via the row signal line Vg1 for each row. The other main terminal of each of a plurality of switch elements 101 (for example, T11, T21, and T31) arrayed in the column direction is electrically connected to a column signal line Sig1 on the first column. While the switch elements 101 are in a conductive state, the switch elements 101 output signals corresponding to the electric charges of the conversion elements to a readout circuit 113 via the column signal line Sig1. Column signal lines Sig1 to Sig3 arrayed in the column direction transfer the signals output from the plurality of pixels PIX in parallel to the readout circuit 113.

The readout circuit 113 is provided, for each column signal line Sig, with an amplification circuit 106 that amplifies the signals output in parallel from the detection unit 112. Each amplification circuit 106 includes an integrating amplifier 105 that amplifies an output electrical signal, a variable amplifier 104 that amplifies the signal input from the integrating amplifier 105, and a sample/hold circuit 107 that samples and holds an amplified signal. The integrating amplifier 105 includes an operational amplifier that amplifies and outputs the signal read out from the pixel PIX, an integrating capacitor, and a reset switch. The integrating amplifier 105 can change the amplification factor by changing the value of the integrating capacitor. The electrical signal output from the pixel PIX is input to the inverting input terminal of the integrating amplifier 105. A reference voltage Vref from a reference power supply 111 is input to the non-inverting input terminal of the integrating amplifier 105. The amplified signal is output from the output terminal of the integrating amplifier 105. An integrating capacitor is arranged between the inverting input terminal and the output terminal of each operational amplifier. The sample/hold circuit 107 includes a sampling switch and a sampling capacitor. The readout circuit 113 includes a multiplexer 108 that sequentially outputs the signals read out in parallel from the respective amplification circuits 106 and outputs the signals as a serial image signal and a buffer amplifier 109 that converts the image signal into impedance and outputs it. An A/D converter 110 converts an image signal Vout as an analog electrical signal output from the buffer amplifier 109 into digital data. For example, digital data during radiation irradiation is output to the computing unit 117 and can be used for exposure control. In addition, for example, digital data after radiation irradiation is output to the control computer 200. The control computer 200 can generate a radiation image by processing the acquired signal.

The radiation image capturing apparatus 100 includes the reference power supply 111 as a power supply unit for each amplification circuit and the bias power supply 103. The reference power supply 111 supplies the reference voltage Vref to the non-inverting input terminal of each operational amplifier. The bias power supply 103 commonly supplies a bias voltage Vs to the conversion elements 102 via the bias wiring Bs.

The drive circuit 114 outputs a drive signal including a conducting voltage Vcom for rendering the switch element 101 conductive and a non-conducting voltage Vss for rendering the switch element 101 non-conductive to a row signal line Vg in accordance with control signals CPV, OE, and DIO input from the control unit 116. With this operation, the drive circuit 114 controls the conductive state and non-conductive state of each switch element 101 and drives the plurality of pixels PIX arranged in the detection unit 112 for each row. The arrangement of the drive circuit 114 and the connection between the control unit 116 and the drive circuits 114 will be described later.

The control signal CPV is a shift clock for a shift register used for a drive circuit. The control signal DIO is a signal for causing the shift register to start a shifting operation in accordance with a shift clock. The control signal OE is a signal for controlling the output terminal of the shift register. In accordance with the control signals CPV, DIO, and OE described above, the control unit 116 sets the time required to drive the detection unit 112 by the drive circuit 114 and a scanning direction. In addition, the control unit 116 supplies control signals RC, SH, and CLK to the readout circuit 113 to control the operation of each constituent element of the readout circuit 113. In this case, the control signal RC serves to control the operation of the reset switch of the integrating amplifier. The control signal SH serves to control the operation of the sample/hold circuit 107. The control signal CLK serves to control the operation of the multiplexer 108.

Figure 3:
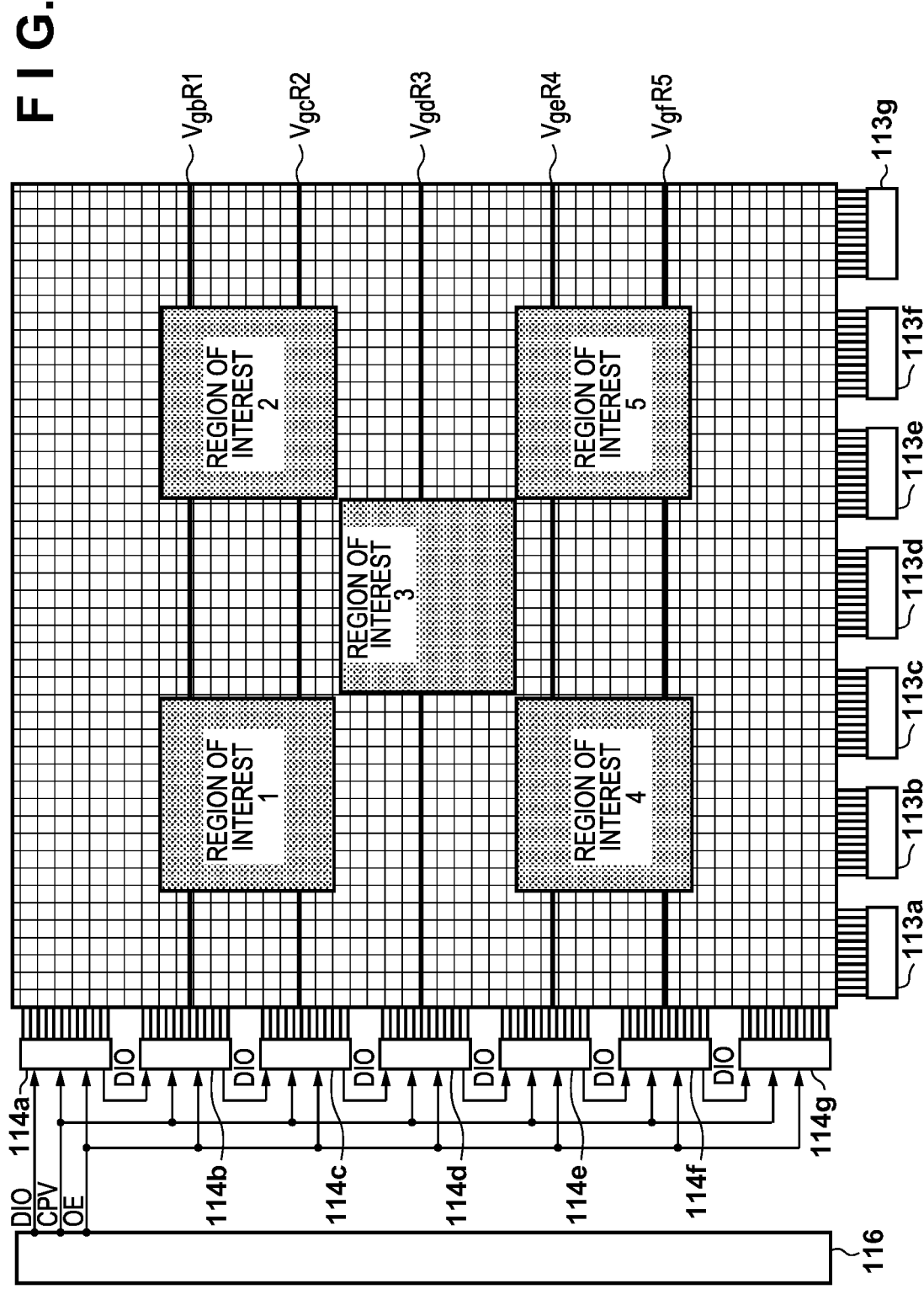
FIG. 3 is an equivalent circuit diagram showing an example of the connection between the control unit and the drive circuits of a radiation image capturing apparatus according to a comparative example.

The connection between the control unit 116 and the drive circuits 114 of the radiation image capturing apparatus 100 and a drive method using AEC (Automatic Exposure Control) will be described next. Before the description of the connection between the control unit 116 and the drive circuits 114 according to this embodiment, a comparative example will be described first. FIG. 3 is an equivalent circuit showing the connection between the control unit 116 and the drive circuits 114 according to the comparative example.

In the arrangement shown in FIG. 3, the radiation image capturing apparatus 100 includes a plurality of (seven) readout circuits 113a to 113g and a plurality of (seven) drive circuits 114a to 114g for one detection unit 112. The plurality of row signal lines Vg for driving the plurality of pixels PIX for each row are respectively connected to the drive circuits 114a to 114g. Signal lines for supplying the control signals CPV and OE from the control unit 116 are respectively connected in parallel with the drive circuits 114a to 114g, and a signal line for supplying the control signal DIO is connected in series with the drive circuits 114a to 114g. That is, the control unit 116 is connected to the drive circuit 114 via the three signal lines.

The detection unit 112 has regions of interest 1 to 5 arranged at coordinates corresponding to the regions of interest in an external AEC chamber. Pixels (to be sometimes referred to as detection pixels hereinafter) used for exposure control are arranged in each of regions of interest 1 to 5. In this case, for the sake of simplicity, assume that there are five regions of interest. However, the number of regions of interest is not limited to this, and four or less or six or more regions of interest may be set. In addition, the positions of the regions of interest are not limited to those shown in FIG. 3, and can be set to arbitrary positions. In this embodiment, detection pixels for exposure control are selected as appropriate from the pixels PIX to obtain a radiation image. However, this is not exhaustive. A plurality of pixels dedicated to AEC may be arranged in the detection unit 112, and arbitrary pixels may be selected from the pixels.

Row signal lines VgbR1 to VgfR5 for respectively controlling the switch elements 101 are connected to the detection pixels arranged in regions of interest 1 to 5. The drive circuit 114b drives the detection pixels in region of interest 1 via the row signal line VgbR1. Likewise, the drive circuit 114c drives the detection pixels in the region of interest 2 via the row signal line VgcR2. The drive circuit 114d drives the detection pixels in region of interest 3 via the row signal line VgdR3. The drive circuit 114e drives the detection pixels in region of interest 4 via the row signal line VgeR4. The drive circuit 114f drives the detection pixels in region of interest 5 via the row signal line VgfR5.

Figure 4:
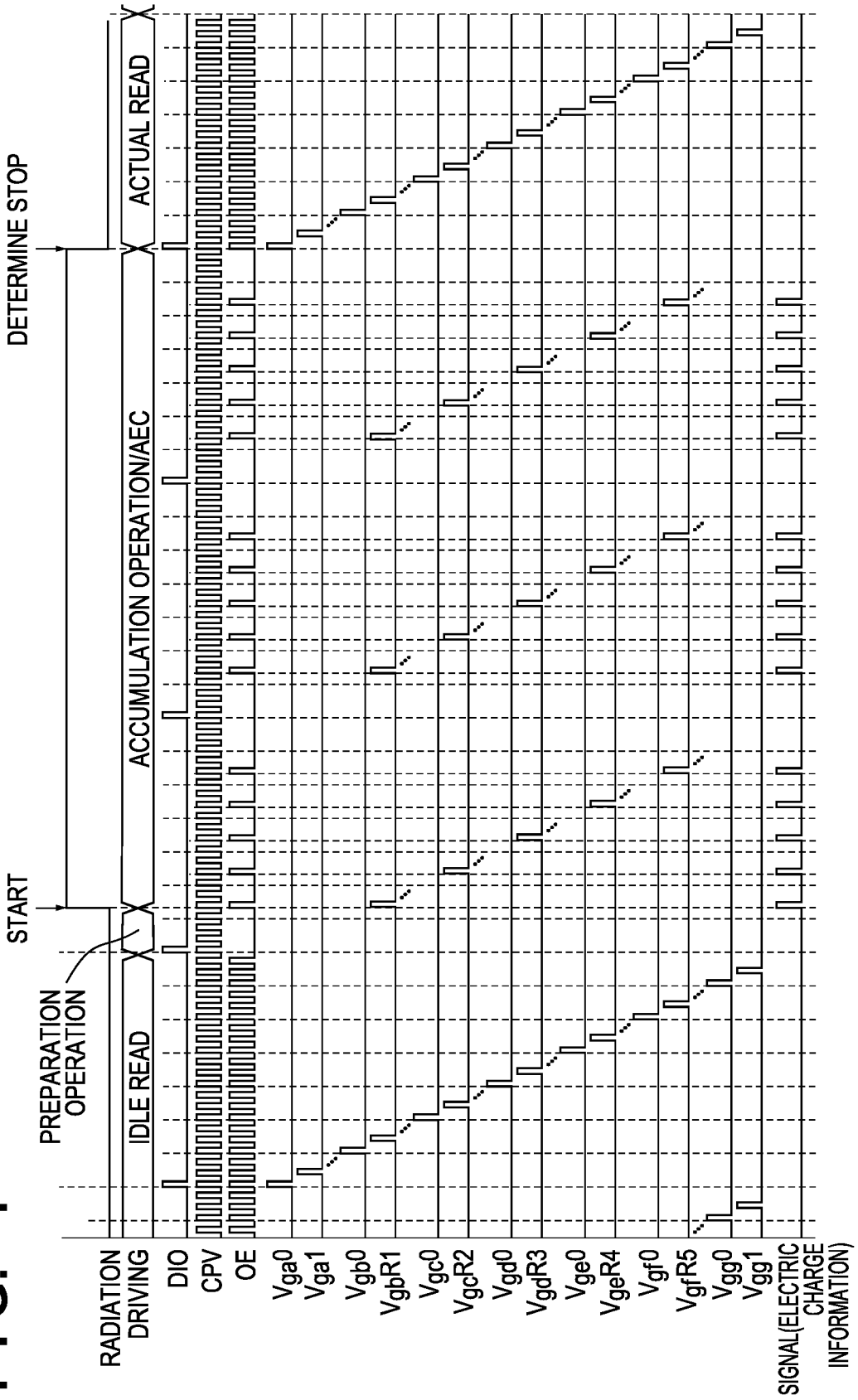
FIG. 4 is a timing chart showing an example of the operation between the control unit and the drive circuits in FIG. 3.
Figure 5:
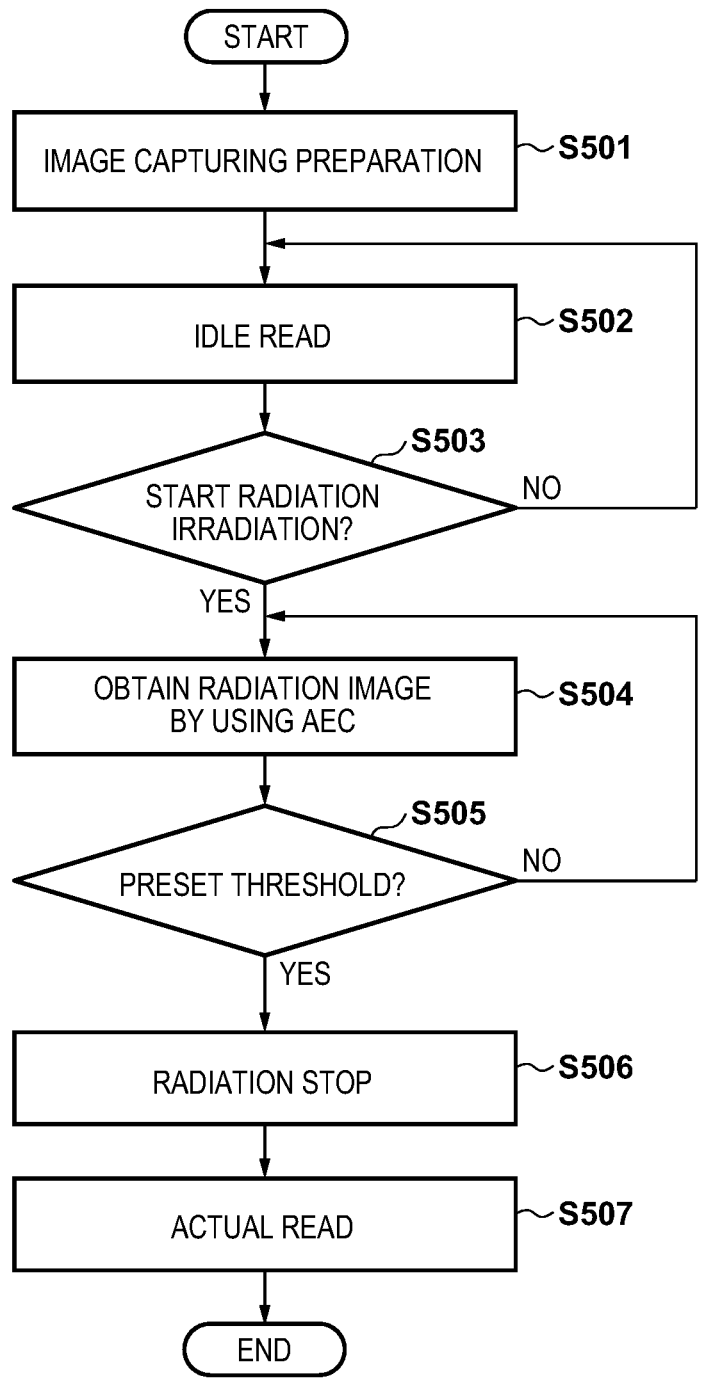
FIG. 5 is a flowchart showing an example of the operation of the radiation image capturing apparatus in FIG. 1.

FIG. 4 is a timing chart showing the operation of the drive circuit 114 according to the comparative example. FIG. 5 is flowchart showing the operation of the radiation image capturing apparatus 100 according to this embodiment and the comparative example. The driving of AEC according to the comparative example will be described with reference to FIGS. 3 to 5.

First of all, when preparation for image capturing is completed in step S501, including setting of conditions for image capturing of a radiation image by the user, the radiation image capturing apparatus 100 shifts the process to step S502. In step S502, the radiation image capturing apparatus 100 starts idle reading. Idle reading is a reset operation of resetting the dark current in each pixel PIX in the detection unit 112 by repeating the ON/OFF operation of the switch element 101 of the pixel PIX. The control unit 116 supplies the control signal DIO to the drive circuit 114a for each frame, and supplies the control signals CPV and OE to each of the drive circuits 114a to 114g to cause them to sequentially scan. In this case, "Vga0" shown in FIG. 4 corresponds to one of the row signal lines connected to the drive circuit 114a shown in FIG. 3. For example, when the drive circuit 114a is a drive circuit for 512 channels, 512 row signal lines including row signal lines Vga0 to Vga511 are connected to the drive circuit 114a to sequentially scan pixels corresponding to 512 channels. The remaining drive circuits 114b to 114g are basically the same as the drive circuit 114a. Detection pixels are sequentially scanned via the row signal lines VgbR1 to VgfR5 to reset the dark currents. The radiation image capturing apparatus 100 performs idle reading until a signal indicating the start of radiation irradiation is input, for example, until the user presses the irradiation switch (step S503).

If an instruction to start radiation irradiation is issued in step S503, for example, if the user presses the irradiation switch, the radiation image capturing apparatus 100 shifts the process to step S504. In step S504, the radiation image capturing apparatus 100 obtains a radiation image by using AEC. As shown in FIG. 4, the control unit 116 performs a preparation operation first, and then performs an accumulation operation. In the preparation operation, the control unit 116 supplies the control signal DIO and the plurality of control signals CPV to the drive circuit 114 to advance the shift register up to the row signal line VgbR1 to which the detection pixels set in region of interest 1 are connected. Upon advancing the shift register up to the row signal line VgbR1 to which the first detection pixel is connected, the control unit 116 transmits an irradiation permit signal notifying the completion of preparation to the control computer 200. In accordance with this irradiation permit signal, the control computer 200 causes the radiation generator 400 to start radiation irradiation via the radiation controller 300. In this embodiment, the radiation image capturing apparatus 100 transmits the irradiation permit signal to the control computer 200. However, the radiation image capturing apparatus 100 may directly transmit the irradiation permit signal to the radiation controller 300. In accordance with this signal, the radiation generator 400 may start radiation irradiation.

Upon starting radiation irradiation, the control unit 116 performs an operation for sequentially reading out signals from the detection pixels arranged in regions of interest 1 to 5. At the same time, the pixels connected to the row signal lines other than those to which the pixels set as detection pixels are connected start accumulation operations for obtaining a radiation image. More specifically, when the control unit 116 outputs the control signal CPV to advance the shift register and the drive circuit 114 selects the row signal lines VgbR1 to VgfR5, the control unit 116 outputs the control signal OE to send signals for turning on the gates of the switch elements 101 of the detection pixels, thereby driving the detection pixels. The control unit 116 then supplies the control signal DIO to the drive circuit 114a for each frame, and repeatedly acquires signals for AEC. At this time, the readout circuit 113 reads out signals (electric charge) corresponding to radiation input from the detection pixels. The computing unit 117 measures the dose of incident radiation based on the signals acquired from the detection pixels. For example, the computing unit 117 adds signals for each detection pixel. When the dose of radiation measured by the computing unit 117 reaches a preset dose, the control unit 116 of the radiation image capturing apparatus 100 transmits a signal for stopping radiation irradiation to the radiation generator 400 for irradiating the radiation image capturing apparatus 100 with radiation. More specifically, when the signal obtained by addition by the computing unit 117 reaches a preset threshold, the control unit 116 transmits an irradiation stop signal to the control computer 200 (step S505). In accordance with this irradiation stop signal, the control computer 200 stops radiation irradiation from the radiation generator 400 via the radiation controller 300 (step S506). In this embodiment, the radiation image capturing apparatus 100 transmits the irradiation stop signal to the control computer 200. However, the radiation image capturing apparatus 100 may directly transmit the irradiation stop signal to the radiation controller 300, and the radiation generator 400 may stop radiation irradiation in accordance with the signal. In addition, when the dose of radiation measured by the computing unit 117 is expected to reach a preset dose, the control unit 116 may transmit the irradiation stop signal to the control computer 200.

Upon completion of radiation irradiation, the control unit 116 performs an actual read operation. The actual read operation is an operation of sequentially applying the conducting voltage Vcom, at which each switch element 101 is turned on, from the drive circuit 114 to the row signal lines Vg, and reading out signals (electric charge) accumulated during radiation irradiation from the conversion elements 102 of the pixels connected to the respective row signal lines to the readout circuit 113. The signals read out to the readout circuit 113 are converted into digital data, which is then transferred as image information to the control computer 200. The control computer 200 generates a radiation image from the acquired image information and displays the image on a display or the like.

Figure 6:
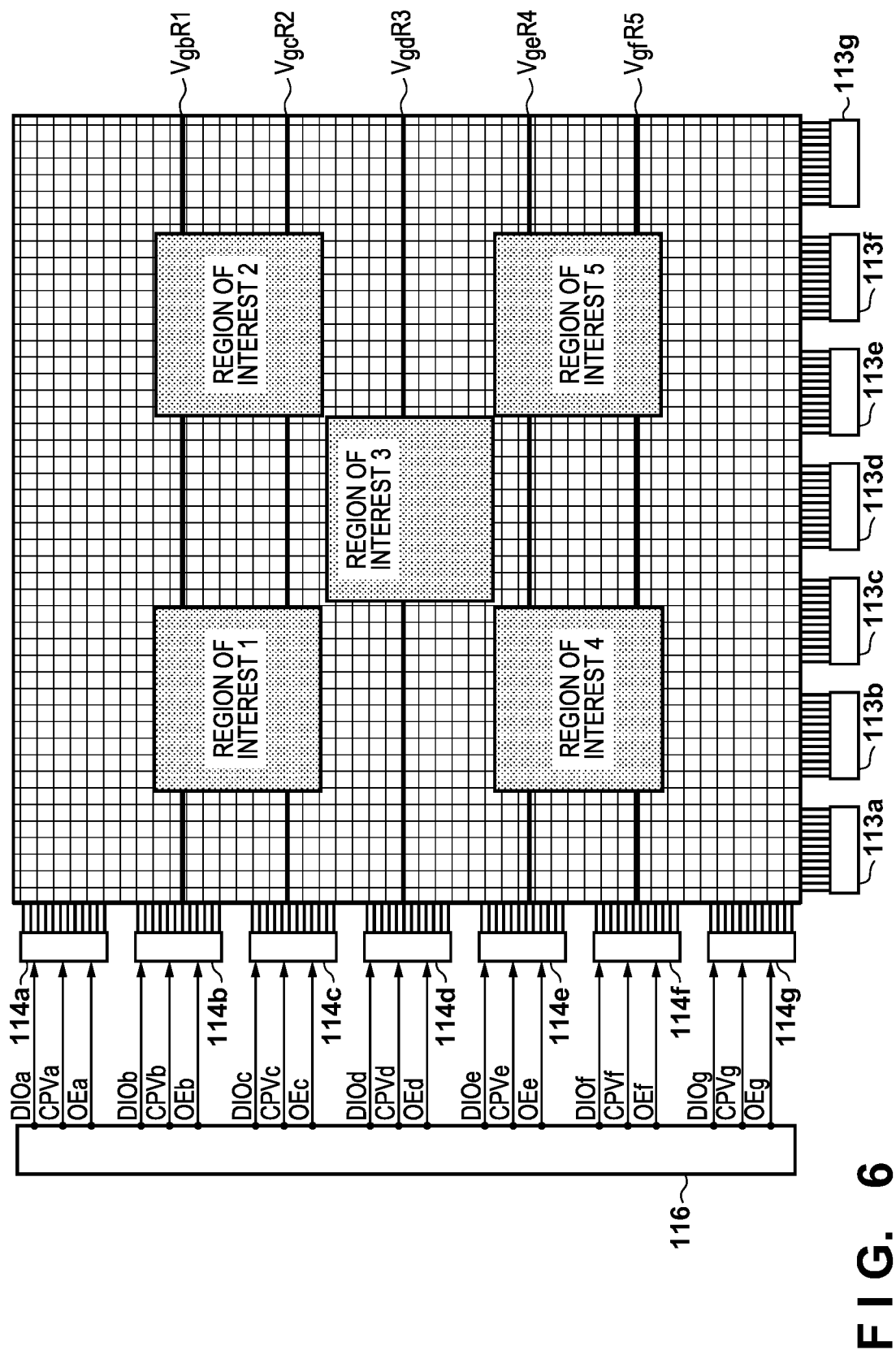
FIG. 6 is an equivalent circuit diagram showing an example of the connection between the control unit and the drive circuits of the radiation image capturing apparatus in FIG. 1.
Figure 7:
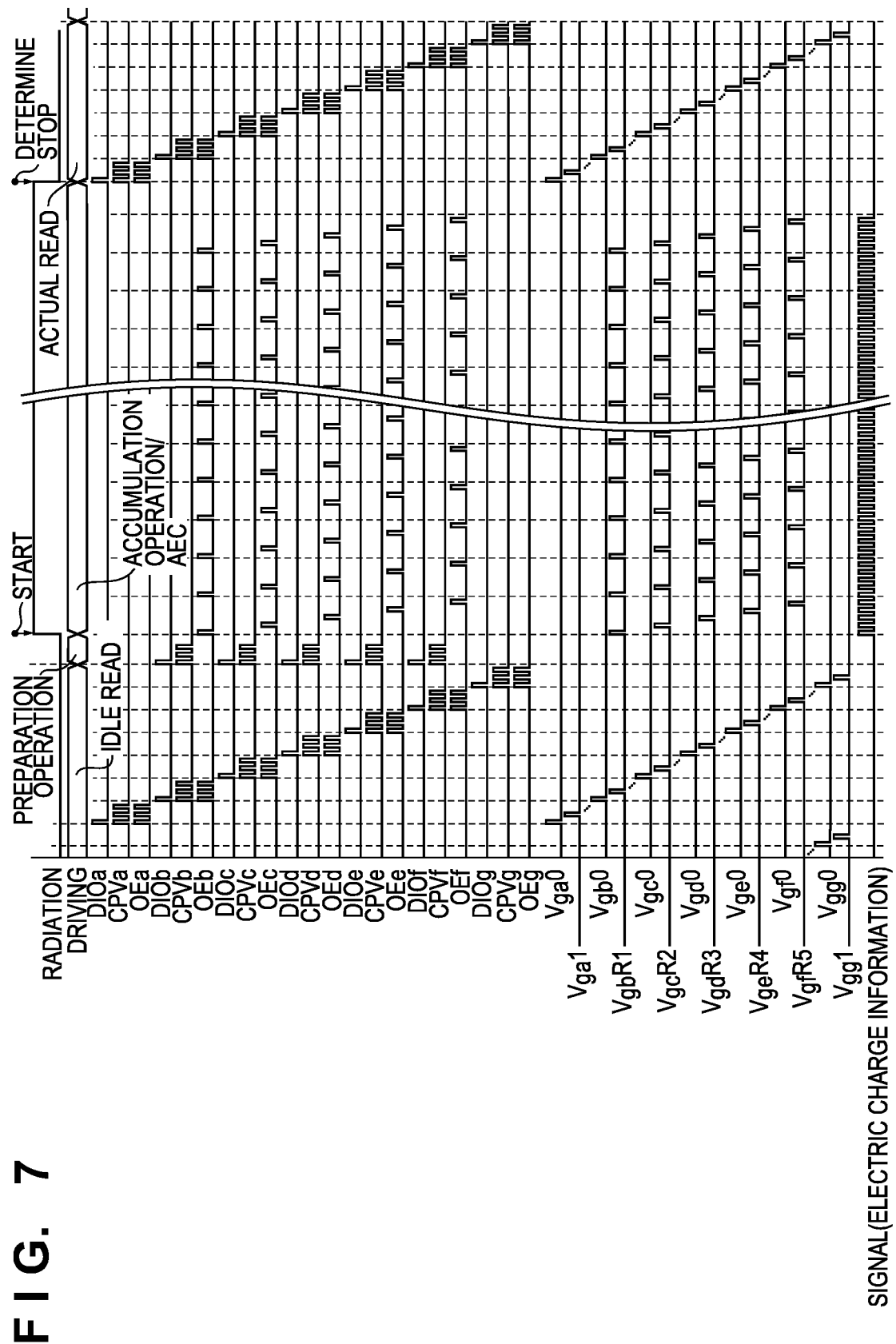
FIG. 7 is a timing chart showing an example of the operation between the control unit and the drive circuits in FIG. 6.
Figure 8:
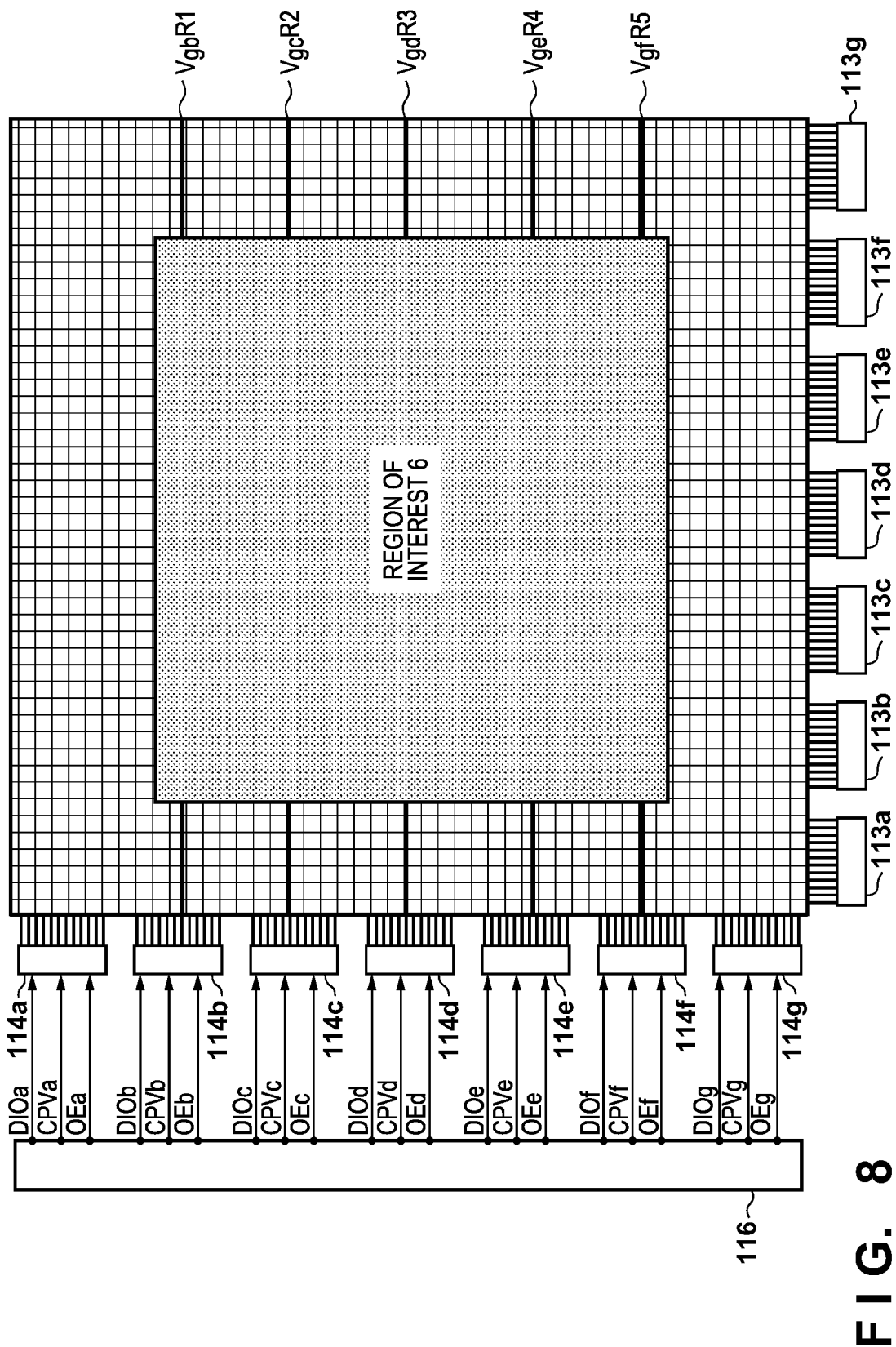
FIG. 8 is a chart showing a modification of the layout of regions of interest in FIG. 6.
Figure 9:
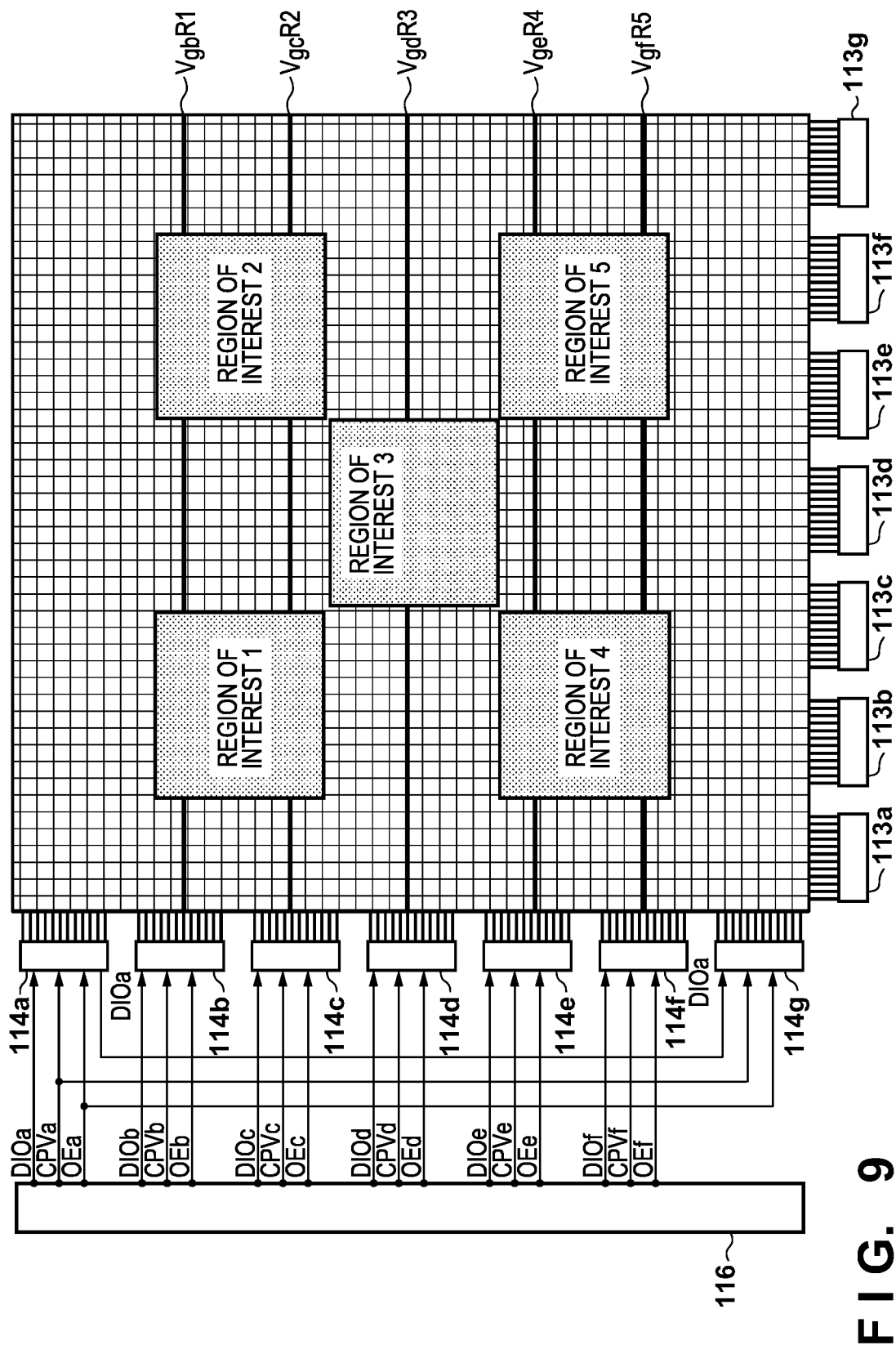
FIG. 9 is an equivalent circuit diagram showing an example of the connection between the control unit and the drive circuits of the radiation image capturing apparatus in FIG. 1.
Figure 10:
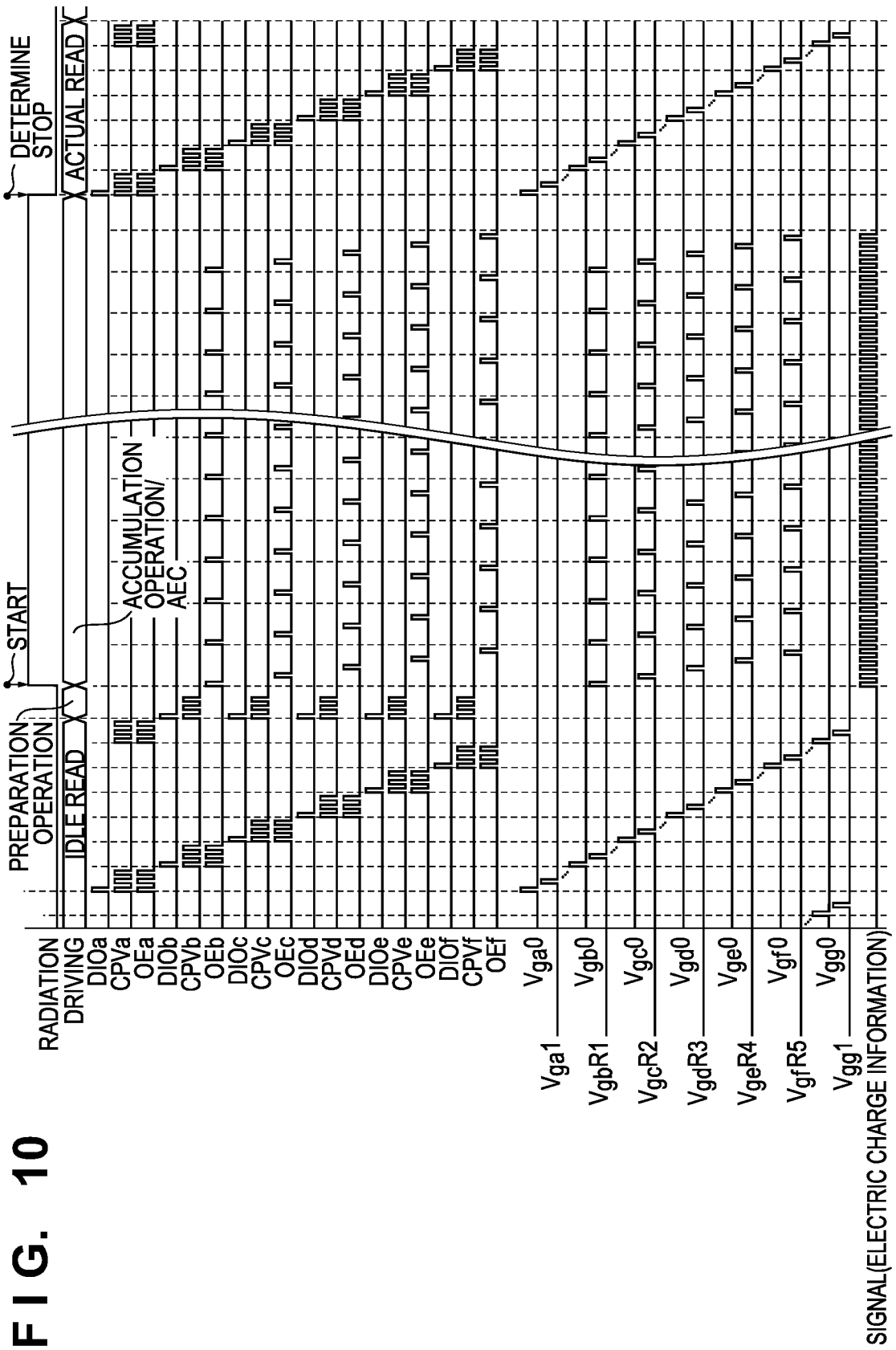
FIG. 10 is a timing chart showing an example of the operation between the control unit and the drive circuits in FIG. 9.
Figure 11:
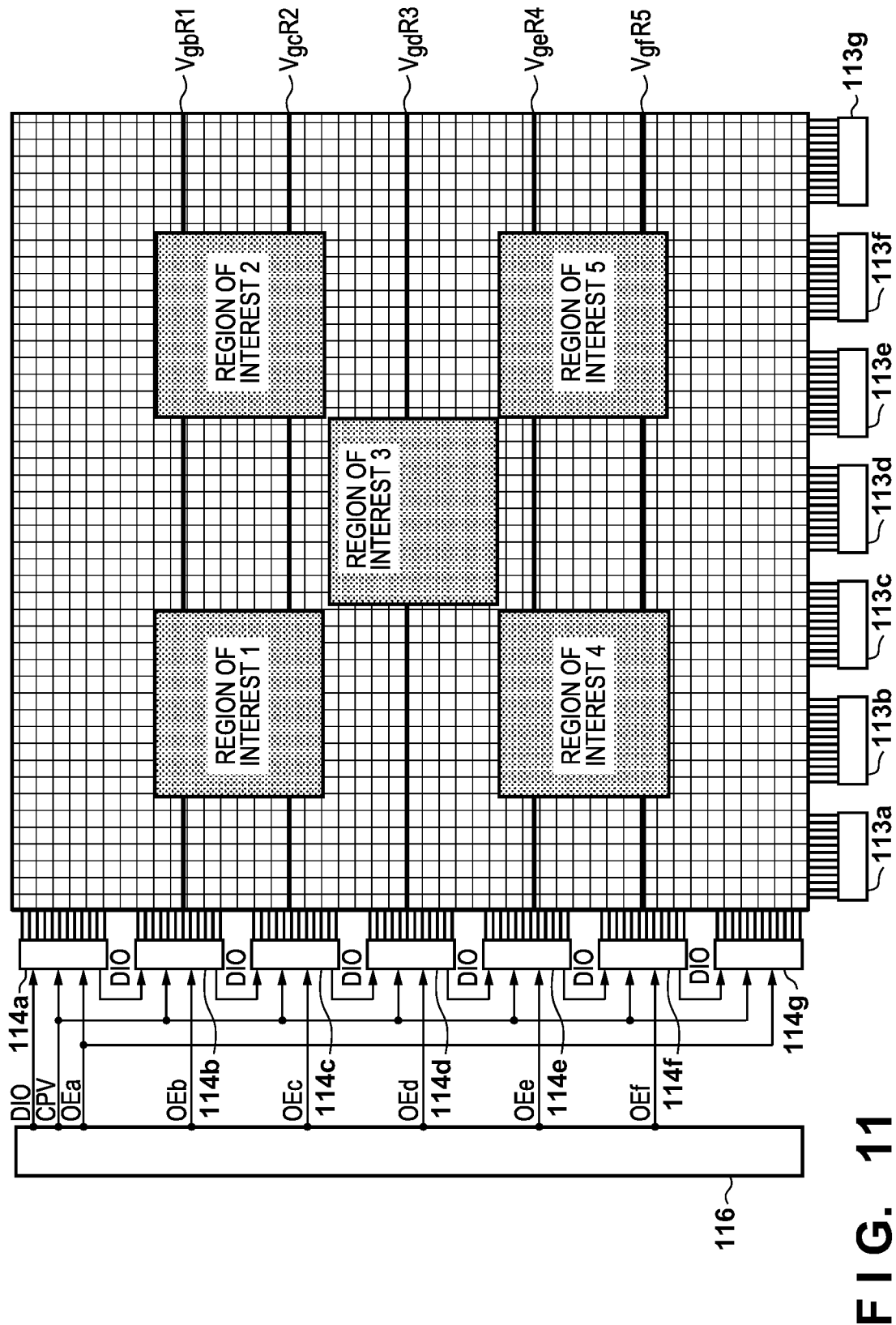
FIG. 11 is an equivalent circuit diagram showing an example of the connection between the control unit and the drive circuits of the radiation image capturing apparatus in FIG. 1.
Figure 12:
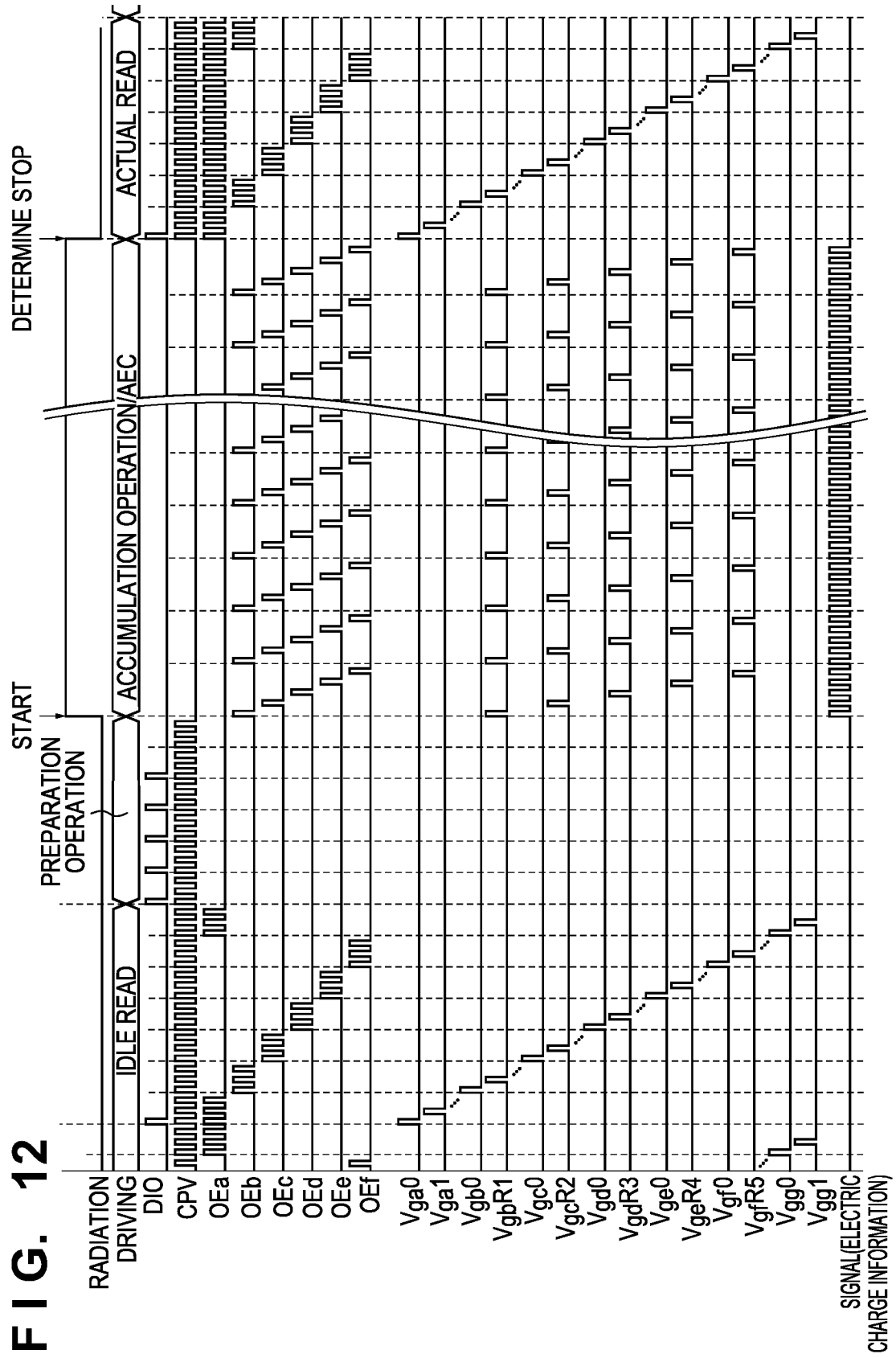
FIG. 12 is a timing chart showing an example of the operation between the control unit and the drive circuits in FIG. 11.

The connection between the control unit 116 and the drive circuits 114 of the radiation image capturing apparatus 100 according to this embodiment and a drive method using AEC will be described next with reference to FIGS. 5 to 12 in comparison with the comparative example. FIGS. 6, 9, and 11 are equivalent circuit diagrams each showing the connection between the control unit 116 and the drive circuits 114 according to the embodiment. FIGS. 7, 10, and 12 are timing charts each showing the operation of the drive circuit 114 in accordance with a corresponding one of the connections shown in FIGS. 6, 9, and 11.

The connection between the control unit 116 and the drive circuits 114 according to this embodiment and the drive method using AEC will be described first with reference to FIGS. 6 and 7. In the comparative Example shown in FIG. 3, the control unit 116 supplies the control signals CPV, DIO, and OE to the drive circuits 114a to 114g via three signal lines respectively corresponding to the control signals CPV, DIO, and OE. In contrast to this, in the embodiment shown in FIG. 6, the control unit 116 supplies control signals CPVa to CPVg, DIOa to DIOg, and OEa to OEg to the seven drive circuits 114a to 114g via three signal lines for each drive circuit, that is, a total of 21 signal lines. That is, the control unit 116 is connected to the drive circuit 114 via the 21 signal lines.

Image capturing of a radiation image is performed in accordance with the flowchart shown in FIG. 5 as in the comparative Example. Upon completion of preparation for image capturing (step S501), the control unit 116 causes the drive circuits 114a to 114g to start idle reading (step S502). At this time, the control unit 116 supplies the control signal DIO to each of the drive circuits 114a to 114g unlike the comparative example. In addition, the control unit 116 inputs the control signals CPV and OE to each of the drive circuits 114a to 114g to cause them to sequentially scan.

If an instruction to start radiation irradiation is issued in step S503, for example, if the user presses the irradiation switch, the radiation image capturing apparatus 100 shifts the process to step S504. In step S504, the radiation image capturing apparatus 100 obtains a radiation image by using AEC. As shown in FIG. 7, the control unit 116 performs a preparation operation first, and then performs an accumulation operation.

The preparation operation in this embodiment will be described in detail. When the process shifts to step S504, the control unit 116 measures the dose of radiation entering from the plurality of pixels PIX during radiation irradiation, and supplies selection signals to a drive circuit group constituted by two or more drive circuits, of the plurality of drive circuits 114a to 114g, which drive detection pixels, to set two or more detection pixels for performing exposure control. More specifically, the control unit 116 outputs the control signals DIOb to DIOf and CPVb to CPVf functioning as selection signals to the drive circuits 114b to 114f, of the drive circuits 114a to 114g, which constitute a drive circuit group to which the detection pixels arranged in regions of interest 1 to 5 are connected. This advances the shift registers of the drive circuits 114b to 114f and causes the drive circuits 114b to 114f included in the drive circuit group to respectively select the row signal lines VgbR1 to VgfR5, of the plurality of row signal lines Vg, to which the detection pixels are connected. At this time, as shown in FIG. 7, the control unit 116 may supply selection signals (control signals DIO and CPV) in parallel to the drive circuits 114b to 114f included in the drive circuit group. This connection relationship allows the control unit 116 to individually supply the control signals DIO and CPV to each of the drive circuits 114a to 114g, and hence the control unit 116 can supply selection signals (control signals DIO and CPV) in parallel to the drive circuits 114b to 114f included in the drive circuit group. This makes it possible to shorten the time required for a preparation operation. Independent signal lines for supplying selection signals (control signals DIO and CPV) are respectively provided for the drive circuits 114a to 114g. This makes it unnecessary for the control unit 116 to supply selection signals (control signals DIO and CPV) to the drive circuits 114a and 114g that are not included in the drive circuit group while the drive circuits 114b to 114f included in the drive circuit group are made to respectively select the row signal lines VgbR1 to VgfR5, of the plurality of row signal lines Vg, to which the detection pixels are connected. Upon completion of the selection of the row signal lines VgbR1 to VgfR5 to which the detection pixels are connected, the control unit 116 transmits an irradiation permit signal for notifying the completion of the preparation to the control computer 200. In accordance with this irradiation permit signal, the control computer 200 causes the radiation generator 400 to start radiation irradiation via the radiation controller 300. As described above, the radiation image capturing apparatus 100 may directly transmit an irradiation permit signal to the radiation controller 300.

Upon starting radiation irradiation, the control unit 116 performs an operation for sequentially reading out signals from the detection pixels arranged in regions of interest 1 to 5. At the same time, the pixels connected to the row signal lines other than those to which the pixels set as the detection pixels are connected start an accumulation operation for obtaining a radiation image. More specifically, during radiation irradiation, the control unit 116 individually supplies the control signals OEb to OEf functioning as drive signals for driving the pixels connected to the row signal lines VgbR1 to VgfR5 selected from the plurality of row signal lines Vg to the drive circuits 114b to 114f included in the drive circuit group. With this operation, the radiation image capturing apparatus 100 acquires signals for exposure control from the respective detection pixels. During radiation irradiation, the control unit 116 does not supply any drive signals (control signals OE) to the drive circuits 114a and 114g that are not included in the drive circuit group (drive circuits 114b to 114f). In addition, during radiation irradiation, because the drive circuits 114b to 114f select the row signal lines VgbR1 to VgfR5 to which the detection pixels are connected, the control unit 116 does not supply any selection signals (control signals DIO and CPV) to the drive circuits 114b to 114f included in the drive circuit group. That is, during radiation irradiation, the control unit 116 need not supply selection signals (control signals DIO and CPV) to all the drive circuits 114a to 114g.

As shown in FIG. 7, the control unit 116 repeats an operation of reading out signals for AEC from the detection pixels by sequential scanning of the control signals OEb to OEg as one frame. That is, the respective detection pixels can be connected to the different drive circuits 114 among the plurality of drive circuits 114a to 114g. At the same time, the readout circuits 113 read out signals (electric charge) corresponding to radiation entering from the detection pixels, and the computing unit 117 adds the acquired signals for each detection pixel. When the signal obtained by addition by the computing unit 117 reaches a preset threshold, the control unit 116 transmits an irradiation stop signal to the control computer 200 (step S505). In accordance with this irradiation stop signal, the control computer 200 stops radiation irradiation from the radiation generator 400 via the radiation controller 300 (step S506). As described above, the radiation image capturing apparatus 100 may directly transmit the irradiation stop signal to the radiation controller 300. A threshold for the transmission of an irradiation stop signal may be common to regions of interest 1 to 5 or may be different among the regions of interest. Such thresholds may be set as appropriate in accordance with conditions for image capturing of radiation images.

Upon completion of radiation irradiation, the control unit 116 performs an actual read operation. The actual read operation is an operation of sequentially applying the conducting voltage Vcom, at which each switch element 101 is turned on, from the drive circuit 114 to the row signal lines Vg, and reading out signals (electric charge) accumulated during radiation irradiation from the conversion elements 102 of the pixels connected to the respective row signal lines into the readout circuit 113. The signals read out into the readout circuit 113 are converted into digital data, which is then transferred as image information to the control computer 200. The control computer 200 generates a radiation image from the acquired image information and displays the image on a display or the like.

The effects of this embodiment will be described below. In the comparative example described above, when signals are read out from the detection pixels for AEC, the shift registers are advanced in series with respect to all the row signal lines Vg of the detection unit 112. In contrast to this, in this embodiment, as shown in FIGS. 6 and 7, the shift registers are advanced in advance to the row signal lines VgbR1 to VgfR5 in a preparation operation, and the drive circuits 114b to 114f are made to select the row signal lines VgbR1 to VgfR5 in advance. This makes it unnecessary to advance the shift registers. Accordingly, during radiation irradiation, it is possible to read out signals for AEC by only supplying the control signals OE to the drive circuits 114b to 114f (drive circuit group).

Consider a case in which when AEC is performed, seven 512-channel drive circuits 114 are used to scan five regions of interest 1 to 5 in the 3584-column detection unit 112. Assume that the supply of the control signals CPV for advancing the shift registers and the supply of the control signals OE for causing the drive circuits 114 to output the conducting voltages Vcom for driving the pixels PIX are regarded as one step. In the comparative example, 3584 steps are required to scan one frame. In contrast to this, in this embodiment, five steps enable to scan one frame. That is, it is possible to read out signals from the detection pixels in a plurality of regions of interest at high speed during radiation irradiation. This can increase the number of readout operations per predetermined dose or irradiation time, thereby enabling AEC with higher accuracy. In addition, the scan time per frame can be shortened, and hence AEC can be performed even if the irradiation time is short.

As described above, this embodiment enables to acquire signals from a plurality of regions of interest at high speed without requiring any complex circuit arrangement with a high degree of freedom in setting regions of interest when performing AEC. This implements the radiation image capturing apparatus 100 that can perform user-friendly AEC with high accuracy.

In this embodiment, upon starting radiation irradiation, the control unit 116 performs an operation of sequentially reading out signals from the detection pixels arranged in regions of interest 1 to 5, and the computing unit 117 adds the signal acquired from each detection pixel. That is, the control unit 116 may determine for each region of interest whether the signal obtained by addition by the computing unit 117 reaches a preset threshold. However, the manner of setting regions of interest is not limited to this. For example, the computing unit 117 may total (average) the signals output from the respective detection pixels in regions of interest 1 to 5, and the control unit 116 may perform exposure control by comparing the totaled (averaged) cumulative value of the signals with a threshold. That is, as shown in FIG. 8, the control unit 116 may determine by using one region of interest 6 including regions of interest 1 to 5 whether the signal obtained by addition by the computing unit 117 reaches a preset threshold. It is possible to selectively use regions of interest 1 to 5 and region of interest 6 as appropriate in accordance with conditions for image capturing of a radiation image. For example, the user may selectively use regions of interest 1 to 5 and region of interest 6 by operating the control computer 200 in step S501. Alternatively, the control unit 116 may select regions of interest 1 to 5 or region of interest 6 in accordance with conditions for image capturing which are input in step S501. For example, exposure control may be performed in accordance with the positioning of a patient such that exposure control is performed by using regions of interest 1 to 5 when the patient is in a standing position and is performed by using region of interest 6 when the patient is in a supine position.

When using region of interest 6, the control unit 116 may perform an operation similar to that shown in FIG. 7. The computing unit 117 adds the signals obtained by totaling or averaging the signals acquired from the respective detection pixels. When the signal obtained by addition by the computing unit 117 reaches a preset threshold, the control unit 116 may transmit an irradiation stop signal to the control computer 200. In addition, when region of interest 6 is used, the signals output from the respective detection pixels can be totalized as described above. Accordingly, even when detection pixels are connected to the same column signal line Sig, signals can be simultaneously read out. The control unit 116 may simultaneously input the control signals OEb to OEf to the drive circuits 114b to 114f and acquire signals for exposure control from the respective detection pixels in one step. That is, during radiation irradiation, the control unit 116 simultaneously supplies drive signals (control signals OE) for driving the pixels connected to the row signal lines selected from the plurality of row signal lines Vg to the drive circuits 114 included in the drive circuit group. This makes it possible to acquire signals for measuring the dose of radiation entering from the respective detection pixels from five detection pixels in one step. As a result, the control unit 116 performs a one-frame operation of reading out signals from the respective detection pixels once in each step, thereby implementing more accurate AEC.

The connection between the control unit 116 and the drive circuits 114 shown in FIGS. 6 and 7 and the drive method using AEC according to the comparative example will be described next with reference to FIGS. 9 and 10. Referring to FIG. 6, as described above, the control unit 116 individually supplies the control signals DIO, CPV, and OE to each of the drive circuits 114a to 114g via three signal lines. That is, the control unit 116 is configured to be able to individually supply a drive signal (control signal OE) and selection signals (control signals DIO and CPV) to each of the plurality of drive circuits 114a to 114g. In contrast to this, in the arrangement shown in FIG. 9, three signal lines are connected from the control unit 116 to each of the five drive circuits 114b to 114f, that is, a total of 15 signal lines are connected from the control unit 116 to the five drive circuits 114a to 114f, which are connected to the pixels PIX in the regions set as regions of interest 1 to 5. In addition, the signal lines for supplying the control signals CPVa and OEa are connected in parallel and the signal line for supplying the control signal DIOa is connected in series to the drive circuits 114a and 114g connected to the pixels PIX in the regions which are not set as regions of interest. That is, the plurality of pixels PIX include pixels that can be set as detection pixels and pixels that cannot be set as detection pixels. In contrast to this, the control unit 116 is configured to be able to individually supply drive signals (control signal OE) and selection signals (control signals DIO and CPV) to each of the drive circuits 114b to 114g, of the plurality of drive circuits 114a to 114g, which drive pixels that can be set as detection pixels.

This configuration can reduce the number of signal lines for supplying control signals and reduce the circuit size and cost in contrast to the connection between the control unit 116 and the drive circuits 114 shown in FIG. 6. This effect increases in particular when a large number of drive circuits 114 are connected to the pixels in regions that are not set as regions of interest.

As shown in FIG. 10, in obtaining a radiation image using AEC in step S504, it is possible to read out signals from the detection pixels arranged in the plurality of regions of interest 1 to 5 as in the connection mode shown in FIG. 6.

In addition, as shown in FIG. 10, the control unit 116 may shorten the time taken for a preparation operation by supplying selection signals (control signals DIO and CPV) in parallel to the drive circuits 114b to 114f included in the drive circuit group.

This can increase the number of readout operations per predetermined dose or irradiation time, thereby enabling AEC with higher accuracy. In addition, the scan time per frame can be shortened, and hence AEC can be performed even if the irradiation time is short. Furthermore, the arrangement shown in FIG. 9 can also use regions of interest 1 to 5 as one region of interest 6 as in the above case. In this case, the control unit 116 may perform an operation similar to that shown in FIG. 10, or may acquire signals for exposure control from the respective detection pixels in one step by simultaneously inputting the control signals OEb to OEf to the drive circuits 114b to 114f.

Another modification of the connection between the control unit 116 and the drive circuits 114 shown in FIGS. 6 and 7 and the drive method using AEC will be described next with reference to FIGS. 11 and 12. The arrangement shown in FIG. 11 uses one signal line for supplying the control signal CPV from the control unit 116 to the drive circuits 114a to 114g in comparison with the arrangement shown in FIG. 6. In addition, this arrangement uses one signal line for supplying the control signal DIO. In contrast, this arrangement is individually provided with signal lines for supplying the control signals OEb to OEf from the control unit 116 to the five drive circuits 114b to 114f connected to the pixels PIX in the regions set as regions of interest 1 to 5. In addition, the signal lines for supplying the control signals OEa are connected in parallel to the drive circuits 114a and 114g connected to the pixels PIX in the regions that are not set as regions of interest. That is, the plurality of pixels PIX include pixels that can be set as detection pixels and pixels that cannot be set as detection pixels. Accordingly, the control unit 116 is configured to be able to individually supply drive signals (control signals OE) to the drive circuits 114b to 114g, of the plurality of drive circuits 114a to 114g, which drive pixels that can be set as detection pixels.

This arrangement increases the number of steps for causing the drive circuits 114b to 114f to select the row signal lines VgbR1 to VgfR5 to which the detection pixels are connected in a preparation operation. However, as compared with the arrangement shown in FIGS. 6 and 8, it is possible to further reduce the number of signal lines for supplying control signals and further reduce the circuit size and cost.

As shown in FIG. 12, in obtaining a radiation image by using AEC in step S504, it is possible to read out signals from the detection pixels arranged in the plurality of regions of interest 1 to 5 at high speed as in the connection mode shown in FIG. 6. This can increase the number of readout operations per predetermined dose or irradiation time, thereby enabling AEC with higher accuracy. In addition, the scan time per frame can be shortened, and hence AEC can be performed even if the irradiation time is short. Furthermore, the arrangement shown in FIG. 11 can also use regions of interest 1 to 5 as one region of interest 6 as in the above case. In this case, the control unit 116 may perform an operation similar to that shown in FIG. 12, or may acquire signals for exposure control from the respective detection pixels in one step by simultaneously inputting the control signals OEb to OEf to the drive circuits 114b to 114f.

A radiation image capturing apparatus according to some embodiments of the present invention will be described with reference to FIGS. 13 to 16. The arrangement of a radiation image capturing apparatus 100 according to this embodiment is the same as that according to the first embodiment described above, and hence a description of the arrangement will be omitted.

Figure 13:
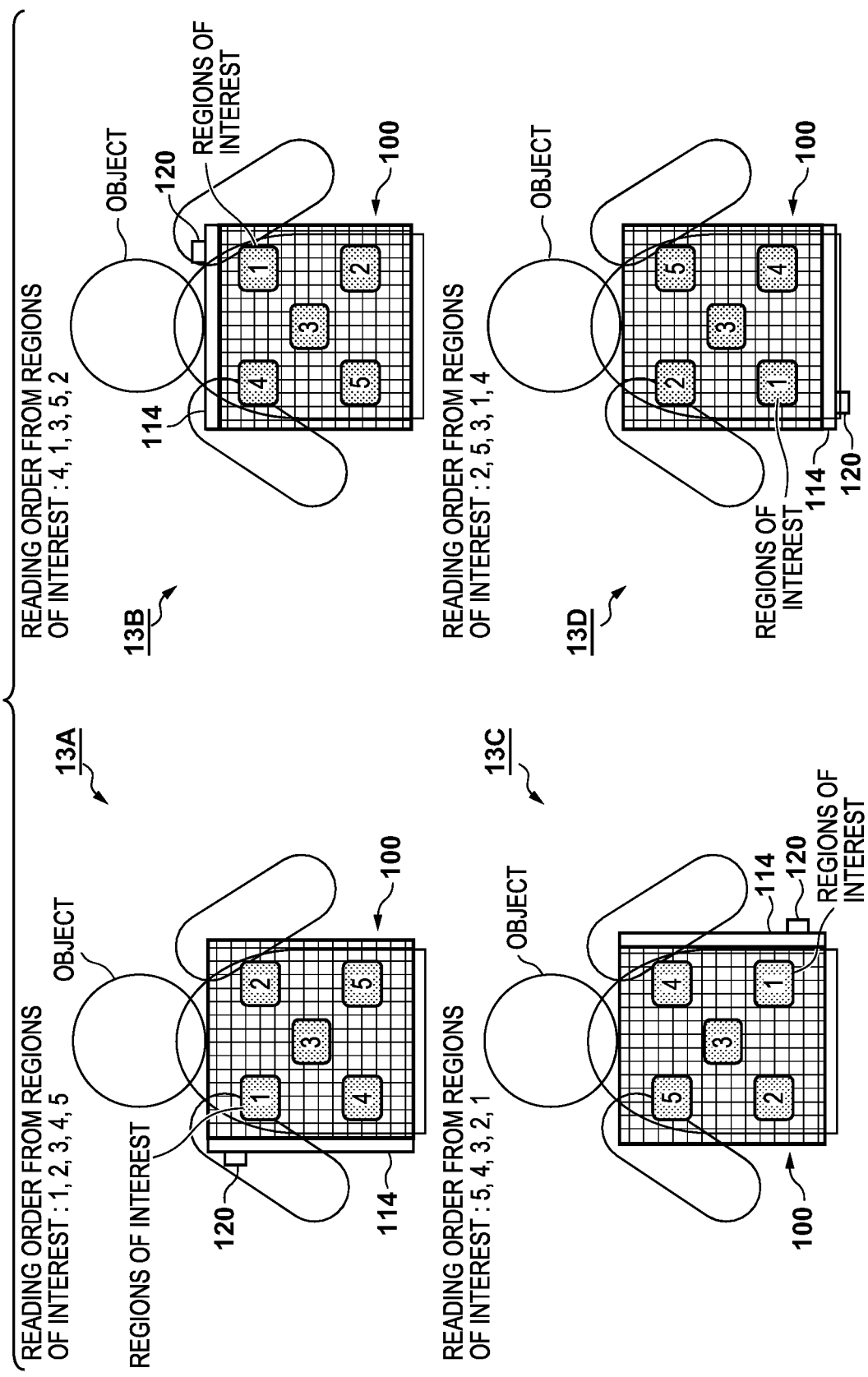
FIG. 13 is a schematic view showing layout examples in the radiation image capturing apparatus in FIG. 1.
Figure 14:
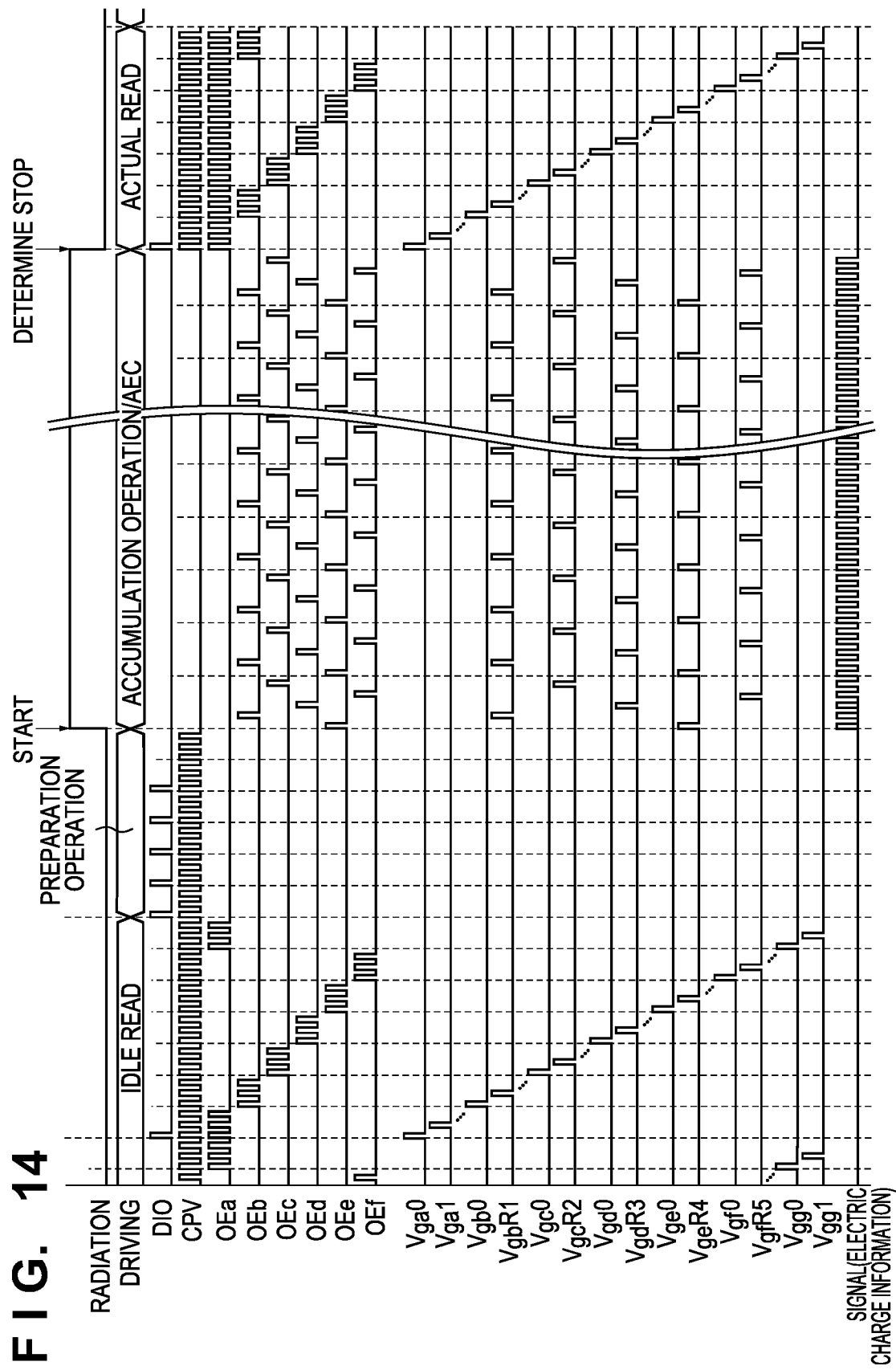
FIG. 14 is a timing chart showing an example of an operation in the layout in FIG. 13.
Figure 15:
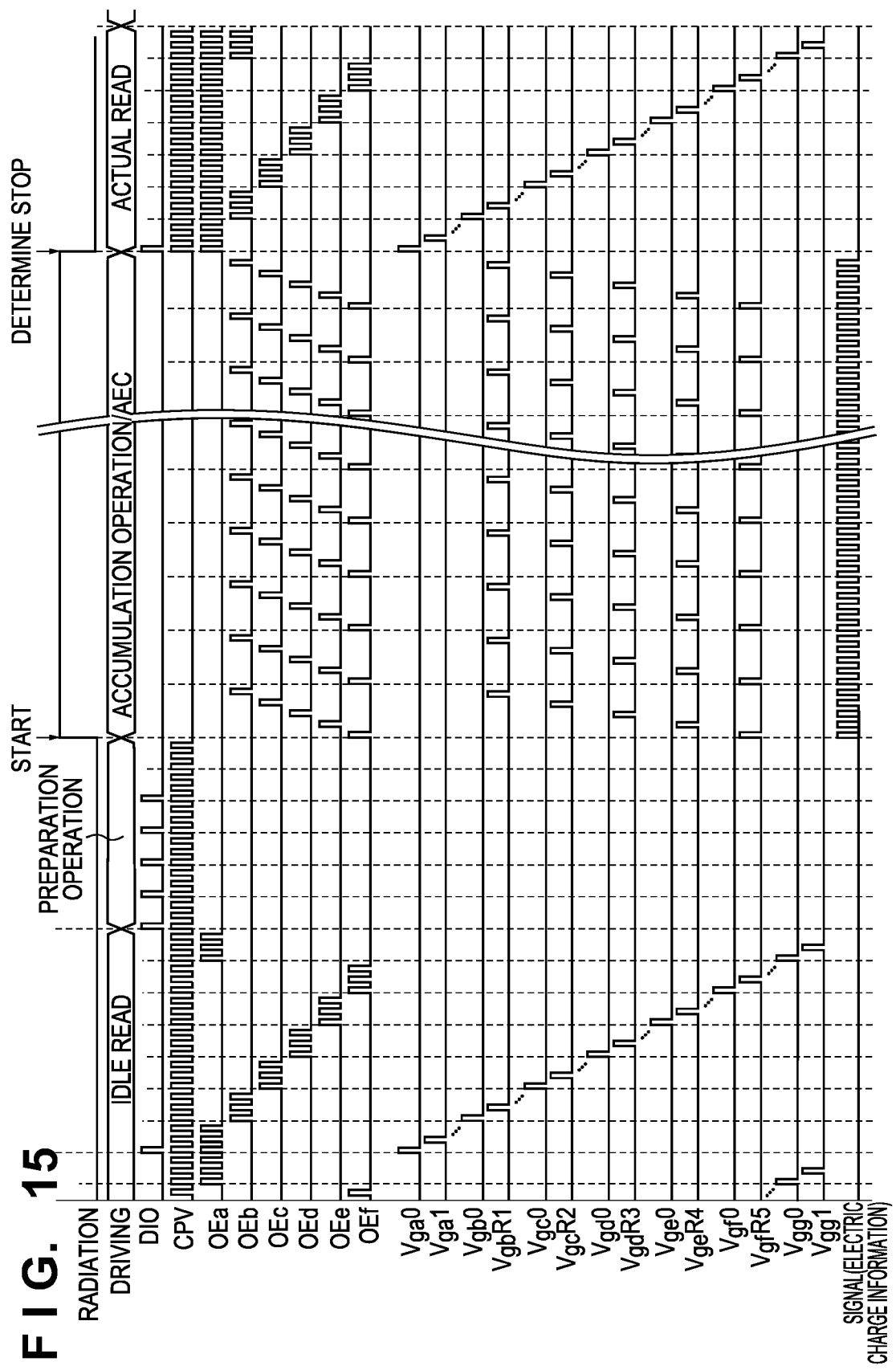
FIG. 15 is a timing chart showing an example of an operation in the layout in FIG. 13.
Figure 16:
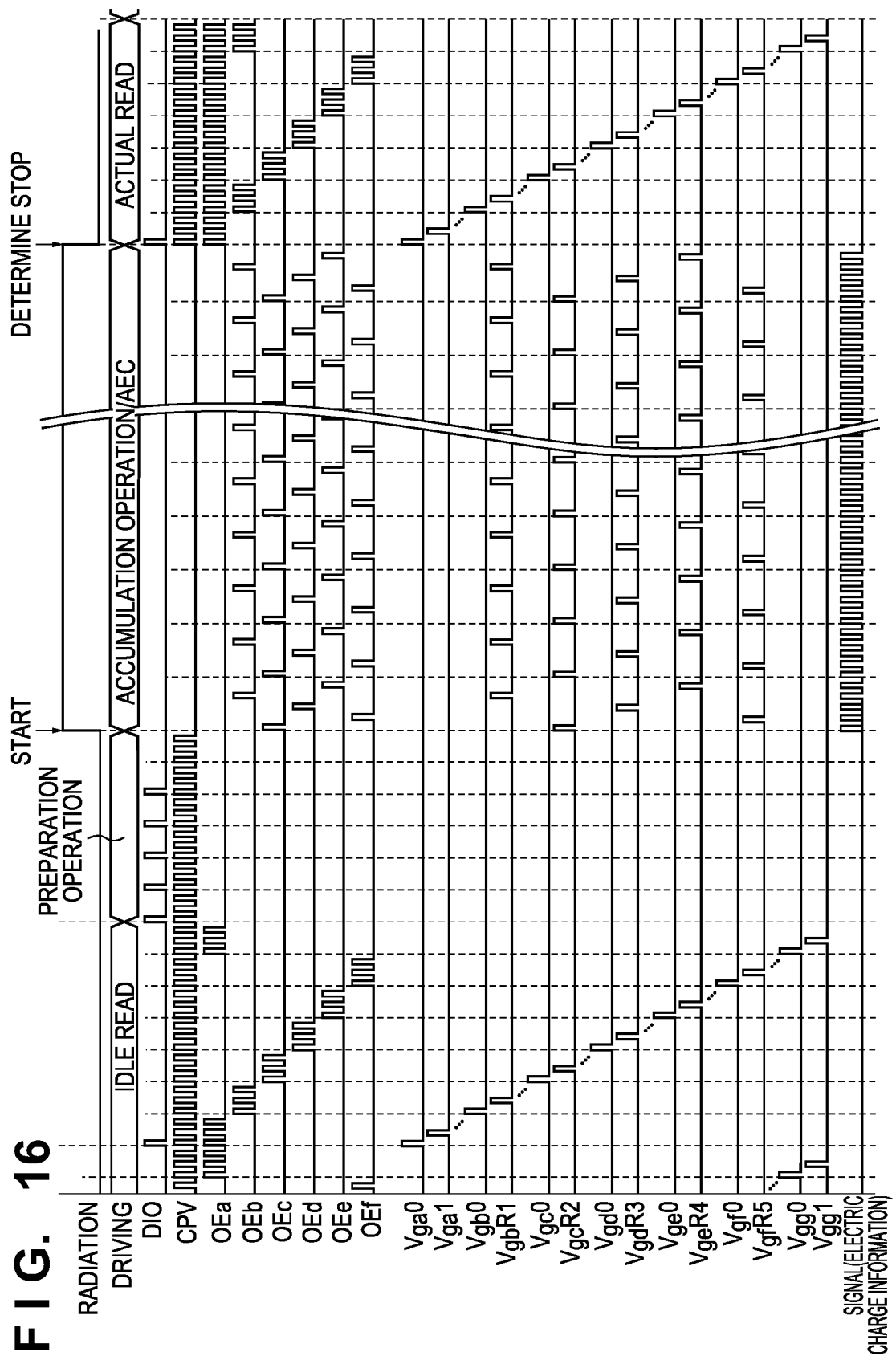
FIG. 16 is a timing chart showing an example of an operation in the layout in FIG. 13.

Layouts 13A to 13D in FIG. 13 are schematic views showing the placement relationship between an object and the radiation image capturing apparatus 100. The radiation image capturing apparatus 100 shown in each of the layouts 13B to 13D is rotated through 90° with respect to the object relative to that shown in the layout 13A. FIGS. 14 to 16 are timing charts each showing the operation of a drive circuit 114 according to this embodiment. An idle read operation, a preparation operation, and an actual read operation can be similar to those in the first embodiment described above, and hence a description of them will be omitted. The timing charts shown in FIGS. 14 to 16 each indicate an operation in the case of the connection between a control unit 116 and drive circuits 114a to 114g shown in FIG. 11.

Assume that in the arrangement shown in the layout 13A, the operation indicated by the timing chart of FIG. 12 described above is performed. In contrast to this, when the object and the radiation image capturing apparatus 100 are arranged in the manner shown in each of the layouts 13B to 13D, the driving operation indicated by a corresponding one of the timing charts of FIGS. 14 to 16 may be performed. More specifically, consider a case in which in the placement relationship shown in the layout 13A, signals are read out from the detection pixels in regions of interest 1, 2, 3, 4, and 5 in this order. In this case, in the placement relationship shown in the layout 13B, the driving operation shown in FIG. 14 may be performed so as to read out signals from the detection pixels in regions of interest 4, 1, 3, 5, and 2 in this order. Likewise, in the placement relationship shown in the layout 13C, the driving operation shown in FIG. 15 may be performed so as to read out signals from the detection pixels in regions of interest 5, 4, 3, 2, and 1 in this order. In addition, in the placement relationship shown in the layout 13D, the driving operation shown in FIG. 16 may be performed so as to read out signals from the detection pixels in regions of interest 2, 5, 3, 1, and 4 in this order. Driving the radiation image capturing apparatus 100 in this manner can read out signals from regions of interest always in a predetermined order with respect to a region of an object, thereby performing AEC with high accuracy.

The user may arbitrarily set an order of reading out signals from regions of interest corresponding to the placement relationship between an object and the radiation image capturing apparatus 100. For example, as shown in the layouts 13A to 13D, the radiation image capturing apparatus 100 may further include a rotation detection unit 120 for detecting the in-plane direction of a detection unit 112 in which a plurality of pixels PIX are arranged. In this case, the control unit 116 may change the order of acquiring signals from detection pixels in accordance with the direction detected by the rotation detection unit 120. The rotation detection unit 120 may independently detect an in-plane direction or may recognize an in-plane direction in accordance with the state of connection with an image capturing table. The control unit 116 may be connected to the drive circuits 114 in any of the arrangements shown in FIGS. 6, 9, and 11.

The order of reading out signals from detection pixels when performing AEC is changed depending on the placement relationship between an object and the radiation image capturing apparatus 100. This makes it possible to acquire signals from a plurality of regions of interest at high speed without requiring any complex circuit arrangement while increasing the degree of freedom in setting regions of interest when performing AEC. This implements the radiation image capturing apparatus 100 that can perform user-friendly AEC with high accuracy.

Figure 17:
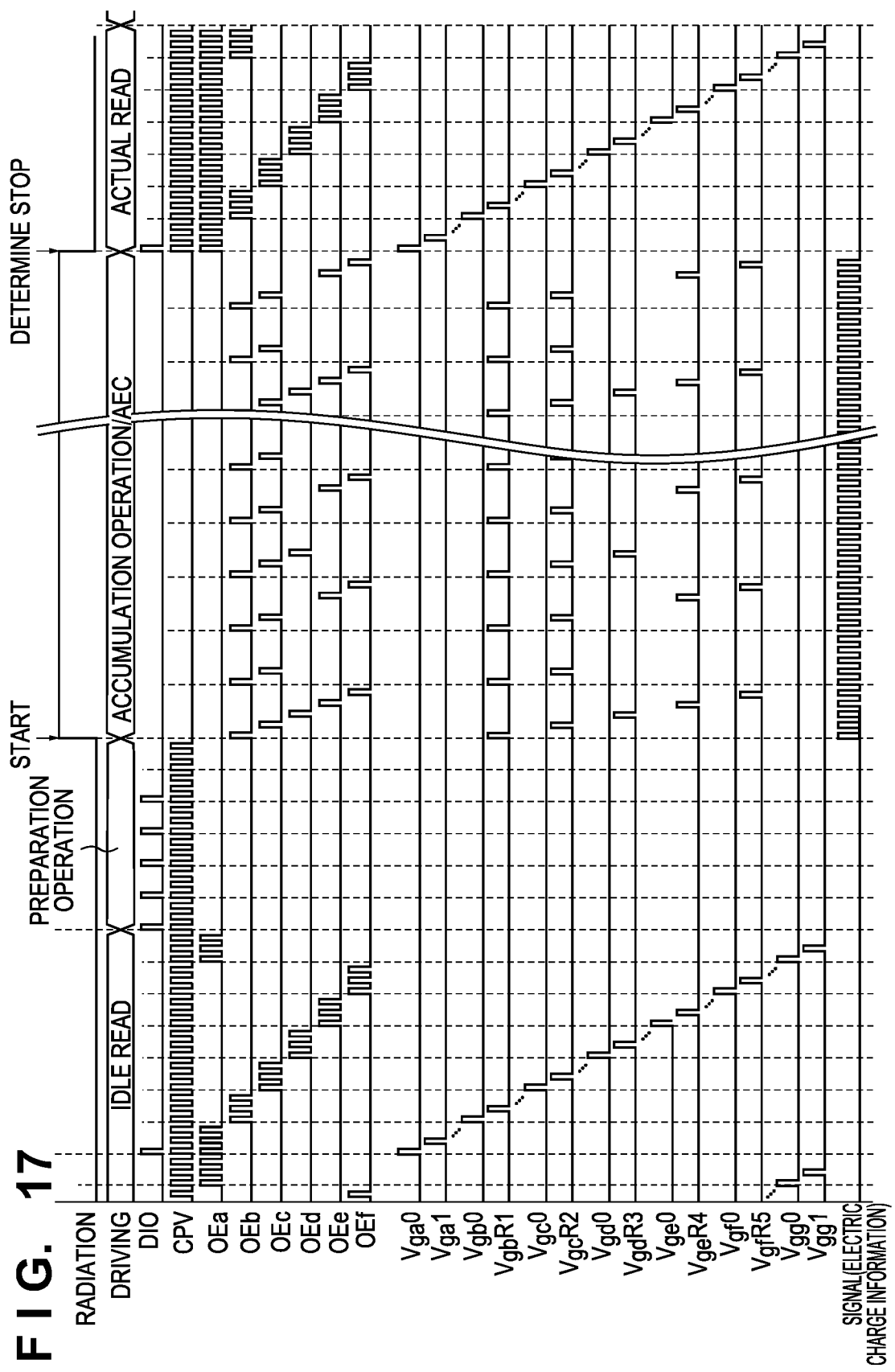
FIG. 17 is a timing chart showing an example of the operation between the control unit and the drive circuits in FIG. 11.

A radiation image capturing apparatus according to some embodiments of the present invention will be described with reference to FIGS. 13 and 17. The arrangement of a radiation image capturing apparatus 100 according to this embodiment is the same as that according to the first embodiment described above, and hence a description of the arrangement will be omitted. FIG. 17 is a timing chart showing the operation of a drive circuit 114 according to this embodiment. An idle read operation, a preparation operation, and an actual read operation can be similar to those in the first embodiment described above, and hence a description of them will be omitted. The timing chart shown in FIG. 17 indicates an operation in the case of the connection between a control unit 116 and drive circuits 114a to 114g shown in FIG. 11.

When the radiation image capturing apparatus 100 is arranged with respect to an object as shown in the layout 13A of FIG. 13, AEC is performed with radiation transmitted through the upper region of the left lung in region of interest 1, the upper region of the right lung in region of interest 2, the backbone in region of interest 3, the left abdominal region in region of interest 4, and the right abdominal region in region of interest 5. In this case, radiation enters the radiation image capturing apparatus 100 in accordance with a transmittance for each region of the object. In general, the relation between the transmittances of the respective regions of an object is represented as follows: upper region of left lung=upper region of right lung>left abdominal region=right abdominal region>backbone. The relation between signal values each obtained per process when signals are read out from detection pixels by the driving operation shown in FIG. 12 can be represented as follows: region of interest 1=region of interest 2>region of interest 4=region of interest 5>region of interest 3. If the signal value obtained per sampling process is large, signals (electric charge information) are sometimes saturated to result in a failure to properly perform determination. In addition, if the pixel value obtained per sampling process is small, signals may be buried in noise to result in a failure to properly determine the end of radiation irradiation.

According to the drive method shown in FIG. 17, the control unit 116 changes the intervals of supplying the control signals OEb to OEf in accordance with regions of interest 1 and 2, region of interest 3, and regions of interest 4 and 5. That is, the detection pixels include, for example, the detection pixels arranged in region of interest 1 and the detection pixels arranged in region of interest 3. During radiation irradiation, the control unit 116 may set different sampling periods at which signals are acquired in accordance with the detection pixels arranged in region of interest 1 and the detection pixels arranged in region of interest 3. When the transmittances of the object are set as follows: upper region of left lung:upper region of right lung:backbone:left abdominal region:right abdominal region=3:3:1:2:2, the control unit 116 sets the intervals of supplying the control signals OEb to OEf as follows: OEb:OEc:OEd:OEf:OEg=3:3:1:2:2. This makes it possible to read out proper signals from the detection pixels arranged in regions of interest 1 to 5 while suppressing the influences of the radiation transmittances of an object.

The user may set a radiation transmittance for each region of interest. In addition, the control unit 116 may automatically recognize radiation transmittances from the signal values of readout signals during image capturing using AEC. The control unit 116 may be connected to the drive circuits 114 in any of the arrangements shown in FIGS. 6, 9, and 11.

This embodiment enables to acquire signals from a plurality of regions of interest at high speed without requiring any complex circuit arrangement with a high degree of freedom in setting regions of interest when performing AEC. This implements the radiation image capturing apparatus 100 that can perform user-friendly AEC with high accuracy.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2019-093913, filed on May 17, 2019, which is hereby incorporated by reference herein in its entirety.

What is claimed is:

1. A radiation image capturing apparatus, comprising:
a plurality of pixels arranged in a matrix pattern configured to obtain a radiation image;
a plurality of drive circuits to which a plurality of row signal lines configured to drive the plurality of pixels for each row are respectively connected; and
a controller connected to the plurality of drive circuits via at least one of the signal lines and configured to control the plurality of drive circuits, wherein
before radiation irradiation the controller supplies selection signals to a drive circuit group comprising at least two of the drive circuits that drive at least two detection pixels to cause each of the drive circuits included in the drive circuit group to select one of the plurality of row signal lines to which the detection pixels are connected in order to set the detection pixels for measuring a dose of radiation entering from the plurality of pixels during radiation irradiation, and
during radiation irradiation the controller supplies a drive signal for driving pixels connected to one of the row signal lines to each drive circuit included in the drive circuit group to cause the radiation image capturing apparatus to acquire a signal for measuring a dose of radiation entering from each of the detection pixels.

2. The apparatus according to claim 1, wherein the controller has is configured to individually supply the drive signal and the selection signal to each drive-circuit of the plurality of drive circuits.

3. The apparatus according to claim 2, wherein the controller is configured to supply the selection signals before radiation irradiation in parallel to drive circuits in the drive circuit group.

4. The apparatus according to claim 1, wherein the plurality of pixels includes a pixel that can be set as the detection pixel and a pixel that cannot be set as the detection pixel, and
the controller is configured to individually supply the drive signal and the selection signal to each of the plurality of drive circuits that drives the pixel that can be set as the detection pixel.

5. The apparatus according to claim 1, wherein the plurality of pixels includes a pixel that can be set as the detection pixel and a pixel that cannot be set as the detection pixel, and
the controller is configured to individually supply the drive signal to each of the plurality of drive circuits that drives the pixel that can be set as the detection pixel.

6. The apparatus according to claim 1, wherein the controller is configured to individually supply the drive signal during radiation irradiation to each drive circuit in the drive circuit group.

7. The apparatus according to claim 1, wherein the controller is configured to simultaneously supply the drive signal during radiation irradiation to each drive circuit in the drive circuit group.

8. The apparatus according to claim 1, wherein the controller is configured not to supply the drive signal during radiation irradiation to any drive circuit that is not included in the drive circuit group.

9. The apparatus according to claim 1, wherein during radiation irradiation the controller does not supply the selection signal to any drive circuit in the drive circuit group.

10. The apparatus according to claim 1, wherein the controller is configured not to supply the selection signal to the plurality of drive circuits during radiation irradiation.

11. The apparatus according to claim 1, wherein the controller is configured to not supply the selection signal to any drive circuit that is not included in the drive circuit group while each drive circuit in the drive circuit group is made to select one of the plurality of row signal lines to which the detection pixel is connected.

12. The apparatus according to claim 1, wherein each of the plurality of drive circuits includes a shift register.

13. The apparatus according to claim 1, wherein the detection pixels are respectively connected to different drive circuits of the plurality of drive circuits.

14. The apparatus according to claim 1, wherein the controller is configured to cause each drive circuit in the drive circuit group to select one of the plurality of row signal lines to which the detection pixel is connected after a user issues an instruction to start radiation irradiation and before radiation irradiation is performed.

15. The apparatus according to claim 14, wherein the controller is configured to perform a reset operation of resetting the plurality of pixels by supplying the selection signal and the drive signal to the plurality of drive circuits before a user issues an instruction to titan radiation irradiation.

16. The apparatus according to claim 1, further comprising a detector rotation provided with the plurality of pixels, wherein
the controller is configured to change an order of acquiring signals from the detection pixels in accordance with a direction of the detector in an in-plane direction.

17. The apparatus according to claim 1, wherein the detection pixels include a first detection pixel and a second detection pixel, and
the controller is configured to change a sampling period in which a signal is acquired during radiation irradiation in accordance with the first detection pixel and the second detection pixel.

18. The apparatus according to claim 1, wherein the radiation image capturing apparatus is configured to transmit a signal for stopping radiation irradiation to a radiation generator for irradiating the radiation image capturing apparatus with radiation to perform exposure control when a dose of radiation measured based on signals acquired from the plurality of pixels reaches a preset dose or is expected to reach the preset dose.

19. A radiation image capturing system, comprising:
the radiation image capturing apparatus according to claim 1; and
a signal processor configured to process a signal from the radiation image capturing apparatus.

* * * * *